(12) United States Patent
Benting et al.

(10) Patent No.: US 9,084,424 B2
(45) Date of Patent: Jul. 21, 2015

(54) N-BENZYL HETEROCYCLIC CARBOXAMIDES

(75) Inventors: Jurgen Benting, Leichlingen (DE); Pierre Cristau, Lyons (FR); Philippe Desbordes, Lyons (FR); Stephanie Gary, Champagne-au-Mont-d'Or (FR); Jorg Greul, Leichlingen (DE); Hendrik Helmke, Liederbach (DE)

(73) Assignee: BAYER INTELLECTUAL PROPERTY GMBH (DE)

( * ) Notice: Subject to any disclaimer, the term of this patent is extended or adjusted under 35 U.S.C. 154(b) by 0 days.

(21) Appl. No.: 13/879,791

(22) PCT Filed: Oct. 20, 2011

(86) PCT No.: PCT/EP2011/068288
§ 371 (c)(1),
(2), (4) Date: Apr. 16, 2013

(87) PCT Pub. No.: WO2012/052490
PCT Pub. Date: Apr. 26, 2012

(65) Prior Publication Data
US 2013/0210864 A1    Aug. 15, 2013

Related U.S. Application Data

(60) Provisional application No. 61/421,033, filed on Dec. 8, 2010.

(30) Foreign Application Priority Data

Oct. 21, 2010   (EP) .................................... 10356028

(51) Int. Cl.
*A61K 31/44* (2006.01)
*A01N 43/56* (2006.01)
*C07D 231/16* (2006.01)
*C07D 401/12* (2006.01)

(52) U.S. Cl.
CPC .............. *A01N 43/56* (2013.01); *C07D 231/16* (2013.01); *C07D 401/12* (2013.01)

(58) Field of Classification Search
USPC .............. 514/341, 406; 548/374.1; 546/275.4
See application file for complete search history.

(56) References Cited

U.S. PATENT DOCUMENTS

| 8,088,927 B2 | 1/2012 | Mansfield et al. | 548/122 |
| 8,324,133 B2 | 12/2012 | Gary et al. | 504/130 |
| 8,410,157 B2 | 4/2013 | Desbordes et al. | 514/406 |
| 2010/0144785 A1 | 6/2010 | Desbordes et al. | 514/307 |
| 2011/0207781 A1 | 8/2011 | Stierli et al. | 514/343 |

FOREIGN PATENT DOCUMENTS

| CN | 1188764 A | 7/1998 |
| CN | 101175750 A | 5/2008 |
| CN | 101360730 A | 2/2009 |
| WO | WO 2006/120224 | * 11/2006 |
| WO | WO 2007/087906 A1 | 8/2007 |
| WO | WO 2009/016220 A1 | 2/2009 |
| WO | WO 2009/016221 | 2/2009 |
| WO | WO 2009/024342 | 2/2009 |
| WO | WO 2009/153191 | 12/2009 |
| WO | WO 2010/130767 | 11/2010 |
| WO | WO 2012/052489 | 4/2012 |
| WO | WO 2012/052491 | 4/2012 |

OTHER PUBLICATIONS

U.S. Appl. No. 13/879,613 corresponding to PCT/EP2011/068287, having an International filing date of Oct. 20, 2011, published as WO 2012/052489 by Jurgen Benting et al.
U.S. Appl. No. 13/880,018 corresponding to PCT/EP2011/068290 having an International filing date of Oct. 20, 2011, published as WO 2012/052491 by Jurgen Benting, et al.
International Search Report issued Dec. 27, 2011 in corresponding International Application No. PCT/EP2011/068288.
U.S. Appl. No. 13/879,613, filed Jun. 12, 2013 by Jürgen Benting et al., entitled 1-(Heterocyclic Carbonyl) Piperidines.
Office Action issued Sep. 2, 2014 in U.S. Appl. No. 13/879,613.

\* cited by examiner

*Primary Examiner* — Rei-Tsang Shiao
(74) *Attorney, Agent, or Firm* — Ostrolenk Faber LLP

(57) ABSTRACT

The present invention relates to N-benzyl heterocyclic carboxamides derivatives or their thiocarboxamides derivatives, their process of preparation, their use as fungicide, particularly in the form of compositions, and methods for the control of phytopathogenic fungi, notably of plants, using these compounds or compositions.

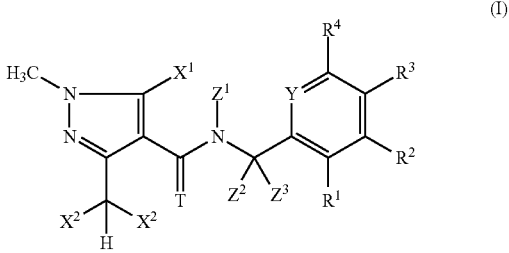

17 Claims, No Drawings

N-BENZYL HETEROCYCLIC CARBOXAMIDES

CROSS REFERENCE TO RELATED APPLICATION(S)

The present application is a 35 U.S.C. §371 national phase conversion of PCT/EP2011/068288 filed on Oct. 20, 2011, which claims priority to European Application No. 10356028.0 filed on Oct. 21, 2010 and U.S. Provisional Application No. 61/421,033 filed on Dec. 8, 2010. Applicants claim priority to the foregoing patent applications. The PCT International Application was published in the English language.

The present invention relates to N-benzyl heterocyclic carboxamides derivatives or their thiocarboxamides derivatives, their process of preparation, their use as fungicides, particularly in the form of compositions, and methods for the control of phytopathogenic fungi, notably of plants, using these compounds or compositions.

In publication J. Korean Agric. Chem. Soc. (1992), 35(2), 87-91 [CAN 117:207009] certain fungicidal amides are generically embraced in the following formula:

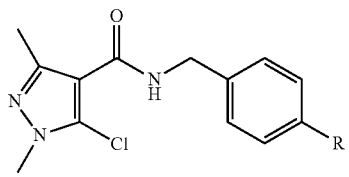

wherein R can represent a hydrogen atom, a chlorine atom, a methyl group or a methoxy group. However, there is no disclosure or suggestion in these documents of any such derivative wherein the 3-substituent of the pyrazolyl group can represent a dihalogenomethyl group. Furthermore, there is no disclosure or suggestion in this document of any compound including an alkyl group, an alkoxy group or a $C_4$-$C_7$-cycloalkyl group linked to the nitrogen atom of the carboxamide residue.

In international patent application WO-2009/024342 certain fungicidal pyrazole-4-carboxylic acid amides are generically embraced in a broad disclosure of numerous compounds of the following formula:

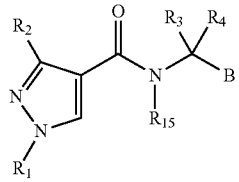

Wherein $R_1$ can represent an alkyl group, $R_2$ can represent a halogenoalkyl group, $R_{15}$ can represent a hydrogen atom or a cyclopropyl group, $R_3$ or $R_4$ can represent various substituents among which an alkyl group, a haloalkyl group and the like, and B can represent a phenyl group, a naphthyl group or a mono or bicyclic heteroaromatic ring system. However, there is no disclosure or suggestion in this document of any such derivative wherein the 5-substituent of the pyrazolyl group can represent a halogen atom. Furthermore, there is no disclosure or suggestion in this document of any compound including an alkyl group, an alkoxy group or a $C_4$-$C_7$-cycloalkyl group linked to the nitrogen atom of the carboxamide residue.

In international patent application CN1188764 certain fungicidal pyrazole derivatives are generically embraced in a broad disclosure of numerous compounds of the following formula:

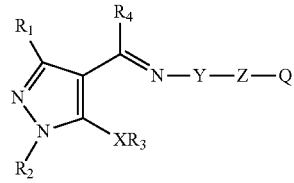

Wherein $R_1$ or $R_2$ can represent an alkyl group or a halogenoalkyl group, X can represent a direct bond, $R_3$ can represent various substituents among which a chlorine atom, $R_4$ can represent various substituents among which an oxygen or a sulfur atom, Y and Z can represent a direct bond, and Q can represent various groups among which a substituted benzyl group. However, there is no disclosure or suggestion in this document of any compound including an alkyl group, an alkoxy group or a $C_4$-$C_7$-cycloalkyl group linked to the nitrogen atom of the carboxamide residue. Furthermore, there is no explicit disclosure or suggestion to select in this document of any such derivative wherein the pyrazolyl group can represent a 1-methyl-3-(difluoro or dichloro)methyl-5-(chloro or fluoro)-4-pyrazolyl group.

In international patent applications WO-2006/120224 and WO-2007/087906, certain amide derivatives are generically embraced in a broad disclosure of numerous compounds of the following formula:

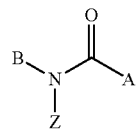

wherein A can represent a carbo-linked, partially saturated or unsaturated, 5-membered heterocyclyl group that can be substituted, Z can represent a(n) (un)substituted cycloalkyl group and B can represent a(n) (un)substituted benzyl group or a substituted 2-pyridylmethylene group. However, there is no disclosure or suggestion in these documents of any compound including a hydrogen atom, an alkyl group or an alkoxy group linked to the nitrogen atom of the carboxamide residue. Furthermore, there is no explicit disclosure or suggestion to select in these documents of any such derivative wherein A can represent a 1-methyl-3-(difluoro or dichloro)methyl-5-(chloro or fluoro)-4-pyrazolyl group.

In international patent applications WO-2009/016221, certain amide derivatives are generically embraced in a broad disclosure of numerous compounds of the following formula:

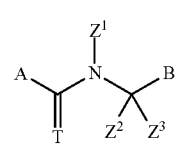

wherein A can represent a carbo-linked, partially saturated or unsaturated, 5-membered heterocyclyl group that can be substituted, T can be O or S, $Z^1$ can represent a(n) (un)substituted cycloalkyl group, $Z^2$ and $Z^3$ can represent a hydrogen atom, a $C_1$-$C_8$-alkyl among other groups, and B can represent a naphthyl group or a bicyclic heteroaromatic group. However, there is no disclosure or suggestion in this document of any compound including a hydrogen atom, an alkyl group or an alkoxy group linked to the nitrogen atom of the carboxamide residue. Moreover, there is no disclosure or suggestion in this document of any compound where B is to be replaced by a phenyl group or a 2-pyridyl group. Furthermore, there is no explicit disclosure or suggestion to select in this document of any such derivative wherein A can represent a 1-methyl-3-(difluoro or dichloro)methyl-5-(chloro or fluoro)-4-pyrazolyl group.

It is always of high interest in agriculture to use novel pesticide compounds in order to avoid or to control the development of resistant strains to the active ingredients. It is also of high interest to use novel compounds being more active than those already known, with the aim of decreasing the amounts of active compound to be used, whilst at the same time maintaining effectiveness at least equivalent to the already known compounds. We have now found a new family of compounds that possess the above mentioned effects or advantages.

Accordingly, the present invention provides derivatives of formula (I)

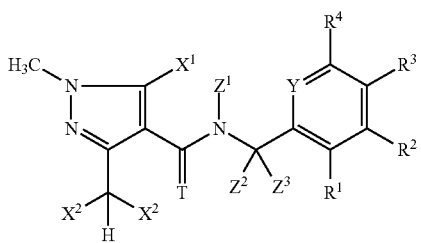

(I)

wherein
Y represents $CR^5$ or N;
T represents O or S;
$X^1$ and $X^2$ which can be the same or different, represent a chlorine or a fluorine atom;
$Z^1$ represents a hydrogen atom, substituted or non substituted $C_1$-$C_8$-alkyl; substituted or non substituted $C_1$-$C_8$-alkoxy; substituted or non substituted $C_2$-$C_8$-alkenyl; substituted or non substituted $C_2$-$C_8$-alkynyl; substituted or non substituted $C_4$-$C_7$-cycloalkyl; substituted or non substituted $C_3$-$C_7$-cycloalkyl-$C_1$-$C_8$-alkyl; substituted or non substituted 3-oxetanyl; or substituted or non substituted 3-thietanyl;
$Z^2$ and $Z^3$, which can be the same or different, represent a hydrogen atom; substituted or non substituted $C_1$-$C_8$-alkyl; substituted or non substituted $C_2$-$C_8$-alkenyl; substituted or non substituted $C_2$-$C_8$-alkynyl; cyano; isonitrile; nitro; a halogen atom; substituted or non substituted $C_1$-$C_8$-alkoxy; substituted or non substituted $C_2$-$C_8$-alkenyloxy; substituted or non substituted $C_2$-$C_8$-alkynyloxy; substituted or non substituted $C_3$-$C_7$-cycloalkyl; substituted or non substituted $C_1$-$C_8$-alkylsulfanyl; substituted or non substituted $C_1$-$C_8$-alkylsulfonyl; substituted or non substituted $C_1$-$C_8$-alkylsulfinyl; amino; substituted or non substituted $C_1$-$C_8$-alkylamino; substituted or non substituted di-$C_1$-$C_8$-alkylamino; substituted or non substituted $C_1$-$C_8$-alkoxycarbonyl; substituted or non substituted $C_1$-$C_8$-alkylcarbamoyl; substituted or non substituted di-$C_1$-$C_8$-alkylcarbamoyl; or substituted or non substituted N—$C_1$-$C_8$-alkyl-$C_1$-$C_8$-alkoxy-carbamoyl; or
$Z^3$ and $R^1$ together with the consecutive carbon atoms to which they are linked form a substituted or non substituted 5-, 6- or 7-membered, partly saturated, carbo- or hetero-cycle comprising up to 3 heteroatoms and $Z^2$ is as herein described; or
$Z^2$ and $Z^3$ together with the carbon atom to which they are linked form a substituted or non substituted $C_3$-$C_7$ cycloalkyl;
$R^1$, $R^2$, $R^3$, $R^4$ and $R^5$, which can be the same or different, represent a hydrogen atom; a halogen atom; nitro; cyano; isonitrile; hydroxyl; sulfanyl; amino; pentafluoro-$\lambda^6$-sulfanyl; substituted or non substituted $C_1$-$C_8$-alkyl; $C_1$-$C_8$-halogenoalkyl comprising up to 9 halogen atoms which can be the same or different; substituted or non substituted $C_1$-$C_8$-alkylamino; substituted or non substituted di-$C_1$-$C_8$-alkylamino; substituted or non substituted $C_1$-$C_8$ alkoxy; $C_1$-$C_8$-halogenoalkoxy comprising up to 9 halogen atoms which can be the same or different; $C_1$-$C_8$-alkoxy-$C_1$-$C_8$-alkyl; substituted or non substituted $C_1$-$C_8$-alkylsulfanyl; $C_1$-$C_8$-halogenoalkylsulfanyl comprising up to 9 halogen atoms which can be the same or different; substituted or non substituted $C_2$-$C_8$-alkenyl; $C_2$-$C_8$-halogenoalkenyl comprising up to 9 halogen atoms which can be the same or different; substituted or non substituted $C_2$-$C_8$-alkynyl; $C_2$-$C_8$-halogenoalkynyl comprising up to 9 halogen atoms which can be the same or different; substituted or non substituted $C_2$-$C_8$-alkenyloxy; $C_2$-$C_8$-halogenoalkenyloxy comprising up to 9 halogen atoms which can be the same or different; substituted or non substituted $C_2$-$C_8$-alkynyloxy; $C_2$-$C_8$-halogenoalkynyloxy comprising up to 9 halogen atoms which can be the same or different; substituted or non substituted $C_3$-$C_7$-cycloalkyl; $C_3$-$C_7$-halogenocycloalkyl comprising up to 9 halogen atoms which can be the same or different; substituted or non substituted $C_3$-$C_7$-cycloalkyl-$C_1$-$C_8$-alkyl; substituted or non substituted $C_3$-$C_7$-cycloalkyl-$C_2$-$C_8$-alkenyl; substituted or non substituted $C_3$-$C_7$-cycloalkyl-$C_2$-$C_8$-alkynyl; substituted or non substituted $C_3$-$C_7$-cycloalkyl-$C_3$-$C_7$-cycloalkyl; substituted or non substituted $C_1$-$C_8$-alkyl-$C_3$-$C_7$-cycloalkyl; formyl; formyloxy; formylamino; carboxy; carbamoyl; N-hydroxycarbamoyl; carbamate; (hydroxyimino)-$C_1$-$C_8$-alkyl; substituted or non substituted $C_1$-$C_8$-alkylcarbonyl; $C_1$-$C_8$-halogenoalkylcarbonyl comprising up to 9 halogen atoms which can be the same or different; substituted or non substituted $C_1$-$C_8$-alkylcarbamoyl; substituted or non substituted di-$C_1$-$C_8$-alkylcarbamoyl; N-(substituted or non substituted $C_1$-$C_8$ alkyloxy)carbamoyl; substituted or non substituted $C_1$-$C_8$-alkoxycarbamoyl; N-(substituted or non substituted $C_1$-$C_8$-alkyl)-(substituted or non substituted $C_1$-$C_8$-alkoxy)-carbamoyl; substituted or non substituted $C_1$-$C_8$-alkoxycarbonyl; $C_1$-$C_8$-halogenoalkoxycarbonyl comprising up to 9 halogen atoms which can be the same or different; substituted or non substituted $C_1$-$C_8$-alkylaminocarbonyl; di-substituted or non substituted $C_1$-$C_8$-alkylaminocarbonyl; substituted or non substituted $C_1$-$C_8$-alkylcarbonyloxy; $C_1$-$C_8$-halogenoalkylcarbonyloxy comprising up to 9 halogen atoms which can be the same or different; substituted or non substituted $C_1$-$C_8$-alkylcarbonylamino; $C_1$-$C_8$-halogenoalkylcarbonylamino comprising up to 9 halogen atoms which can be the same or different; substituted or non substituted $C_1$-$C_8$-alkylaminocarbonyloxy; substituted or non substituted di-$C_1$-$C_8$-alkylaminocarbonyloxy; substituted or non substituted $C_1$-$C_8$ alkyloxycarbonyloxy; substituted or non substituted $C_1$-$C_8$-alkylsulfinyl; $C_1$-$C_8$-halogenoalkylsulfinyl comprising up to 9 halogen atoms which can be the same or different; substituted or non substituted $C_1$-$C_8$-alkylsulfonyl; $C_1$-$C_8$-halogenoalkylsulfonyl comprising up to 9 halogen atoms which can be the same or different; substituted or non substituted $C_1$-$C_8$ alkoxyimino; ($C_1$-$C_8$-alkoxyimino)-$C_1$-$C_8$-alkyl; substituted or non substituted ($C_1$-$C_8$-alkenyloxyimino)-$C_1$-$C_8$-alkyl; ($C_1$-$C_8$-alkynyloxyimino)-$C_1$-$C_8$-alkyl; a (benzyloxyimino)-$C_1$-$C_8$-alkyl; tri(substituted or non substituted $C_1$-$C_8$-alkyl)silyl; tri(substituted or non substituted $C_1$-$C_8$-alkyl)silyl-$C_1$-$C_8$-alkyl; benzyloxy which can be substituted by up to 5 groups Q; benzylsulfanyl which can be substituted by up to 5 groups Q; benzylamino which can be substituted by up to 5 groups Q; aryl which can be substituted by up to 7 groups Q; aryloxy which can be substituted by up to 7 groups Q; arylamino which can be substituted by up to 7 groups Q; arylsulfanyl which can be substituted by up to 7 groups Q; aryl-$C_1$-$C_8$alkyl which can be substituted by up to 7 groups Q; aryl-$C_2$-$C_8$-alkenyl which can be substituted by up to 7 groups Q; aryl-$C_2$-$C_8$-alkynyl which can be substituted by up to 7 groups Q; pyridinyl which can be substituted by up to 4 groups Q; pyridinyloxy which can be substituted by up to 4 groups Q; aryl-$C_3$-$C_7$-cycloalkyl which can be substituted by up to 7 groups Q; or Two vicinal substituents R together with the consecutive carbon atoms to which they are linked form a substituted or non substituted 5- or 6-membered, saturated, carbo- or hetero-cycle comprising up to 3 heteroatoms and the other substituents R are as herein-described; or $R^1$ and $Z^3$ together with the consecutive carbon atoms to which they are linked form a substituted or non substituted 5-, 6- or 7-membered, partly saturated, carbo- or hetero-cycle comprising up to 3 heteroatoms, and $R^2$ to $R^5$ are as herein-described;

Q, which can be the same or different, represents a halogen atom; cyano; nitro; $C_1$-$C_8$-alkyl; $C_1$-$C_8$-alkoxy; $C_1$-$C_8$-alkylsulfanyl; $C_1$-$C_8$-halogenoalkyl comprising up to 9 halogen atoms which can be the same or different; $C_1$-$C_8$-halogenoalkoxy comprising up to 9 halogen atoms which can be the same or different; tri($C_1$-$C_8$) alkylsilyl or tri($C_1$-$C_8$)alkylsilyl-$C_1$-$C_8$-alkyl;

as well as salts, N-oxides, metal complexes, metalloid complexes and optically active or geometric isomers thereof.

Unless indicated otherwise, a group or a substituent that is substituted according to the invention can be substituted by one or more of the following groups or atoms: a halogen atom; nitro; hydroxyl; cyano; isonitrile; amino; thio; a pentafluoro-$\lambda^6$-sulfanyl group; formyl; formyloxy; formylamino; carbamoyl; N-hydroxycarbamoyl; carbamate; (hydroxyimino)-$C_1$-$C_6$-alkyl; $C_1$-$C_8$-alkyl; a tri($C_1$-$C_8$-alkyl) silyl; $C_3$-$C_8$-cycloalkyl; $C_1$-$C_8$-halogenoalkyl having 1 to 5 halogen atoms; a $C_3$-$C_8$-halogenocycloalkyl having 1 to 5 halogen atoms; $C_2$-$C_8$-alkenyl; $C_2$-$C_8$-alkynyl; $C_2$-$C_8$-alkenyloxy; $C_2$-$C_8$-alkynyloxy; $C_1$-$C_8$-alkylamino; di-$C_1$-$C_8$-alkylamino; $C_1$-$C_8$-alkoxy; $C_1$-$C_8$-halogenoalkoxy having 1 to 5 halogen atoms; $C_1$-$C_8$-alkylsulfanyl; $C_1$-$C_8$-halogenoalkylsulfanyl having 1 to 5 halogen atoms; $C_2$-$C_8$-alkenyloxy; $C_2$-$C_8$-halogenoalkenylwry having 1 to 5 halogen atoms; $C_3$-$C_8$-alkynyloxy; $C_3$-$C_8$-halogenoalkynyloxy having 1 to 5 halogen atoms; $C_1$-$C_8$-alkylcarbonyl; $C_1$-$C_8$-halogenoalkylcarbonyl having 1 to 5 halogen atoms; $C_1$-$C_8$-alkylcarbamoyl; di-$C_1$-$C_8$-alkylcarbamoyl; N—$C_1$-$C_8$-alkyloxycarbamoyl; $C_1$-$C_8$-alkoxycarbamoyl; N—$C_1$-$C_8$-alkyl-$C_1$-$C_8$-alkoxycarbamoyl; $C_1$-$C_8$-alkoxycarbonyl; $C_1$-$C_8$-halogenoalkoxycarbonyl having 1 to 5 halogen atoms; $C_1$-$C_8$-alkylcarbonyloxy; $C_1$-$C_8$-halogenoalkylcarbonyloxy having 1 to 5 halogen atoms; $C_1$-$C_8$-alkylcarbonylamino; $C_1$-$C_8$-halogenoalkylcarbonylamino having 1 to 5 halogen atoms; $C_1$-$C_8$-alkylaminocarbonyloxy; di-$C_1$-$C_8$-alkylaminocarbonyloxy; $C_1$-$C_8$-alkyloxycarbonyloxy; $C_1$-$C_8$-alkylsulfanyl; $C_1$-$C_8$-halogenoalkylsulfanyl having 1 to 5 halogen atoms; $C_1$-$C_8$-alkylsulfinyl; $C_1$-$C_8$-halogenoalkylsulfinyl having 1 to 5 halogen atoms; $C_1$-$C_8$-alkylsulfonyl; $C_1$-$C_8$-halogenoalkyl-sulfonyl having 1 to 5 halogen atoms; $C_1$-$C_8$-alkylaminosulfamoyl; di-$C_1$-$C_8$-alkylaminosulfamoyl; ($C_1$-$C_6$-alkoxyimino)-$C_1$-$C_6$-alkyl; ($C_1$-$C_6$-alkenyloxyimino)-$C_1$-$C_6$-alkyl; ($C_1$-$C_6$-alkynyloxyimino)-$C_1$-$C_6$-alkyl; 2-oxopyrrolidin-1-yl; (benzyloxyimino)-$C_1$-$C_6$-alkyl; $C_1$-$C_8$-alkoxyalkyl; $C_1$-$C_8$-halogenoalkoxyalkyl having 1 to 5 halogen atoms; benzyloxy; benzylsulfanyl; benzylamino; aryloxy; arylsulfanyl or arylamino.

Any of the compounds according to the invention can exist as one or more stereoisomers depending on the number of stereogenic units (as defined by the IUPAC rules) in the compound. The invention thus relates equally to all the stereoisomers, and to the mixtures of all the possible stereoisomers, in all proportions. The stereoisomers can be separated according to the methods that are known per se by the man ordinary skilled in the art.

According to the invention, the following generic terms are generally used with the following meanings:
  halogen means fluorine, chlorine, bromine or iodine;
  heteroatom can be nitrogen, oxygen or sulfur;
  any alkyl, alkenyl or alkynyl group can be linear or branched;
  the term "aryl" means phenyl or naphthyl, optionally substituted;
  In the case of an amino group or the amino moiety of any other amino-comprising group, substituted by two substituents that can be the same or different, the two substituents together with the nitrogen atom to which they are linked can form a heterocyclyl group, preferably a 5- to 7-membered heterocyclyl group, that can be substituted or that can include other hetero atoms, for example a morpholino or piperidinyl group.

Preferred compounds of formula (I) according to the invention are those wherein Y represents $CR^5$.

Other preferred compounds of formula (I) according to the invention are those wherein Y represents N.

Other preferred compounds of formula (I) according to the invention are those wherein T represents 0.

Other preferred compounds of formula (I) according to the invention are those wherein $X^1$ represents a fluorine atom.

Other preferred compounds of formula (I) according to the invention are those wherein $X^2$ represents a fluorine atom.

Other preferred compounds of formula (I) according to the invention are those wherein $Z^1$ represents a hydrogen atom.

Other preferred compounds of formula (I) according to the invention are those wherein $Z^1$ represents a methyl or an ethyl.

Other preferred compounds of formula (I) according to the invention are those wherein $Z^1$ represents a unsubstituted cyclobutyl.

Other preferred compounds of formula (I) according to the invention are those wherein $Z^2$ and $Z^3$ independently represent a hydrogen atom or a methyl.

More preferred compounds of formula (I) according to the invention are those wherein $Z^2$ represents a hydrogen atom and $Z^3$ represents a hydrogen atom or a methyl.

Other preferred compounds of formula (I) according to the invention are those wherein $R^1$, $R^2$, $R^3$, $R^4$ and $R^5$, which can be the same or different, represent a hydrogen atom; a halogen atom; substituted or non substituted $C_1$-$C_8$-alkyl; $C_1$-$C_8$-halogenoalkyl comprising up to 9 halogen atoms which can be the same or different; substituted or non substituted $C_3$-$C_7$-cycloalkyl; tri($C_1$-$C_8$-alkyl)silyl; or substituted or non substituted $C_1$-$C_8$-alkylsulfanyl.

More preferred compounds of formula (I) according to the invention are those wherein the substituent $R^1$ represents a halogen atom; $C_1$-$C_8$-alkyl; $C_1$-$C_8$-halogenoalkyl comprising up to 9 halogen atoms which can be the same or different; $C_3$-$C_7$-cycloalkyl; tri($C_1$-$C_8$-alkyl)silyl or $C_1$-$C_8$-halogenoalkylsulfanyl comprising up to 9 halogen atoms which can be the same or different.

Other more preferred compounds of formula (I) according to the invention are those wherein the substitutents $R^1$ and $R^5$, which can be the same or different, represent a halogen atom; $C_1$-$C_8$-alkyl; $C_1$-$C_8$-halogenoalkyl comprising up to 9 halogen atoms which can be the same or different; $C_3$-$C_7$-cycloalkyl; tri($C_1$-$C_8$-alkyl)silyl or $C_1$-$C_8$-halogenoalkylsulfanyl comprising up to 9 halogen atoms which can be the same or different.

The above mentioned preferences with regard to the substituents of the compounds of formula (I) according to the invention can be combined in various manners, either individually, partially or entirely. These combinations of preferred features thus provide sub-classes of compounds according to the invention. Examples of such sub-classes of preferred compounds according to the invention can combine:
preferred features of T with preferred features of one or more $X^1$, $X^2$, Y, $Z^1$ to $Z^3$, and/or $R^1$ to $R^5$;
preferred features of $X^1$ with preferred features of one or more T, $X^2$, Y, $Z^1$ to $Z^3$, and/or $R^1$ to $R^5$;
preferred features of $X^2$ with preferred features of one or more T, $X^1$, Y, $Z^1$ to $Z^3$, and/or $R^1$ to $R^5$;
preferred features of Y with preferred features of one or more T, $X^1$, $X^2$, $Z^1$ to $Z^3$, and/or $R^1$ to $R^5$;
preferred features of $Z^1$ with preferred features of one or more T, $X^1$, $X^2$, Y, $Z^2$, $Z^3$, and/or $R^1$ to $R^5$;
preferred features of $Z^2$ with preferred features of one or more T, $X^1$, $X^2$, Y, $Z^1$, $Z^3$, and/or $R^1$ to $R^5$;
preferred features of $Z^3$ with preferred features of one or more T, $X^1$, $X^2$, Y, $Z^1$, $Z^2$, and/or $R^1$ to $R^5$;
preferred features of $R^1$ with preferred features of one or more T, $X^1$, $X^2$, Y, $Z^1$ to $Z^3$, and/or $R^2$ to $R^5$;
preferred features of $R^2$ with preferred features of one or more T, $X^1$, $X^2$, Y, $Z^1$ to $Z^3$, $R^1$, and/or $R^3$ to $R^5$;
preferred features of $R^3$ with preferred features of one or more T, $X^1$, $X^2$, Y, $Z^1$, to $Z^3$, $R^1$, $R^2$, $R^4$, and/or $R^5$;
preferred features of $R^4$ with preferred features of one or more T, $X^1$, $X^2$, Y, $Z^1$ to $Z^3$, $R^1$ to $R^3$, and/or $R^5$;
preferred features of $R^5$ with preferred features of one or more T, $X^1$, $X^2$, Y, $Z^1$ to $Z^3$, and/or $R^1$ to $R^4$;
In these combinations of preferred features of the substituents of the compounds according to the invention, the said preferred features can also be selected among the more preferred features of each of T, $X^1$, $X^2$, Y, $Z^1$ to $Z^3$, and $R^1$ to $R^5$; so as to form most preferred subclasses of compounds according to the invention.

The present invention also relates to a process for the preparation of the compound of formula (I). Thus, according to a further aspect of the present invention there is provided a process P1 for the preparation of a compound of formula (I) as herein defined and wherein T represents O and that comprises reaction of a N-substituted amine derivative of formula (II) or one of its salts:

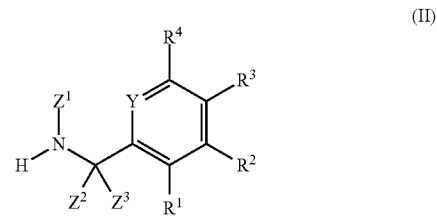

(II)

wherein $Z^1$, $Z^2$, $Z^3$, Y, $R^1$, $R^2$, $R^3$ and $R^4$ are as herein-defined; with a carboxylic acid derivative of formula (III):

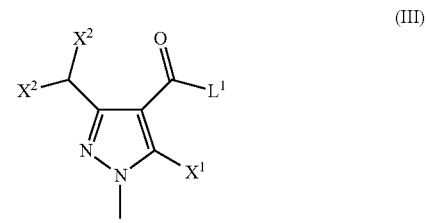

(III)

wherein $X^1$ and $X^2$ are as herein defined and $L^1$ represents a leaving group selected in the list consisting of a halogen atom, a hydroxyl group, —$OR^a$, —OC(=O)$R^a$, $R^a$ being a substituted or non-substituted $C_1$-$C_6$-alkyl, a substituted or non-substituted $C_1$-$C_6$-haloalkyl, a benzyl, a 4-methoxybenzyl or a pentafluorophenyl group; in the presence of a catalyst and in the presence of a condensing agent in case $L^1$ represents a hydroxyl group, and in the presence of an acid binder in case $L^1$ represents a halogen atom.

N-substituted amine derivatives of formula (II) are known or can be prepared by known processes such as reductive amination of aldehydes or ketones (Bioorganics and Medicinal Chemistry Letters (2006), 16, 2014), or reduction of imines (Tetrahedron (2005), 61, 11689), or nucleophilic substitution of a halogen, mesylate or tosylate (Journal of Medicinal Chemistry (2002), 45, 3887).

Carboxylic acid derivatives of formula (III) can be prepared according to process P2.

In case $L^1$ represents a hydroxy group, the process according to the present invention is conducted in the presence of a condensing agent. Suitable condensing agents may be selected in the non limited list consisting of acid halide former, such as phosgene, phosphorous tribromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenyl-phosphine/tetrachloromethane, 4-(4,6-dimethoxy[1.3.5]-triazin-2-yl)-4-methylmorpholinium chloride hydrate, bromotripyrrolidinophosphonium hexafluorophosphate or propanephosphonic anhydride (T3P).

The process according to the present invention is conducted in the presence of a catalyst. Suitable catalyst may be selected in the list consisting of 4-dimethyl-aminopyridine, 1-hydroxy-benzotriazole or dimethylformamide.

In case $L^1$ represents a halogen atom, the process according to the present invention is conducted in the presence of an acid binder. Suitable acid binders for carrying out process P1 according to the invention are in each case all inorganic and organic bases that are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as cesium carbonate, sodium carbonate, potassium carbonate, potassium bicarbonate, sodium bicarbonate, alkali metal or alkaline earth metal acetates, such as sodium acetate, potassium acetate, calcium acetateand also tertiary amines, such as trimethylamine, triethylamine, diisopropylethylamine, tributylamine, N,N-dimethylaniline, pyridine, N-methylpiperidine, N,N-dimethylaminopyridine, diazabicyclooctane (DABCO), diazabicyclo-nonene (DBN) or diazabicycloundecene (DBU). It is also possible to work in the absence of an additional condensing agent or to employ an excess of the amine component, so that it simultaneously acts as acid binder agent.

According to a further aspect according to the invention, there is provided a process P2 for the preparation of carboxylic acid derivatives of formula (III) wherein T represents O and illustrated according to the following reaction scheme:

Step 3 of process P2 is performed in the presence of a fluorinating agent, and if appropriate in the presence of a solvent.

Step 4 of process P2 is performed in the presence of an acid or a base and if appropriate in the presence of a solvent Suitable oxidants for carrying out step 1 of process P2 according to the invention are in each case all inorganic and organic oxidant which are customary for such reactions. Preference is given to using benzyltriethylammonium permanganate, bromine, chlorine, m-chloroperbenzoic acid, chromic acid, chromium (VI) oxide, hydrogen peroxide, hydrogen peroxide-boron trifluoride, hydrogen peroxide-urea, 2-hydroxyperoxyhexafluoro-2-propanol; Iodine, oxygen-platinum catalyst, perbenzoic acid, peroxyacetyl nitrate, potassium permanganate, potassium ruthenate, pyridinium dichromate, ruthenium (VIII) oxide, silver (I) oxide, silver (II) oxide, silver nitrite, sodium chlorite, sodium hypochlorite, or 2,2,6,6-tetramethylpiperidin-1-oxyl.

Suitable acid halides for carrying out steps 2 and 5 of process P2 according to the invention are in each case all organic or inorganic acid halides which are customary for such reactions. Preference is given to using notably phosgene, phosphorous trichloride, phosphorous pentachloride, phosphorous trichloride oxide, thionyl chloride, or carbon tetrachloride-triphenylphosphine.

Suitable fluorinating agents for carrying out step 3 of process P2 according to the invention is in each case all fluorinating agents which are customary for such reactions. Preference is given to using caesium fluoride, potassium fluoride, potassium fluoride-calcium difluoride, or tetrabutylammonium fluoride.

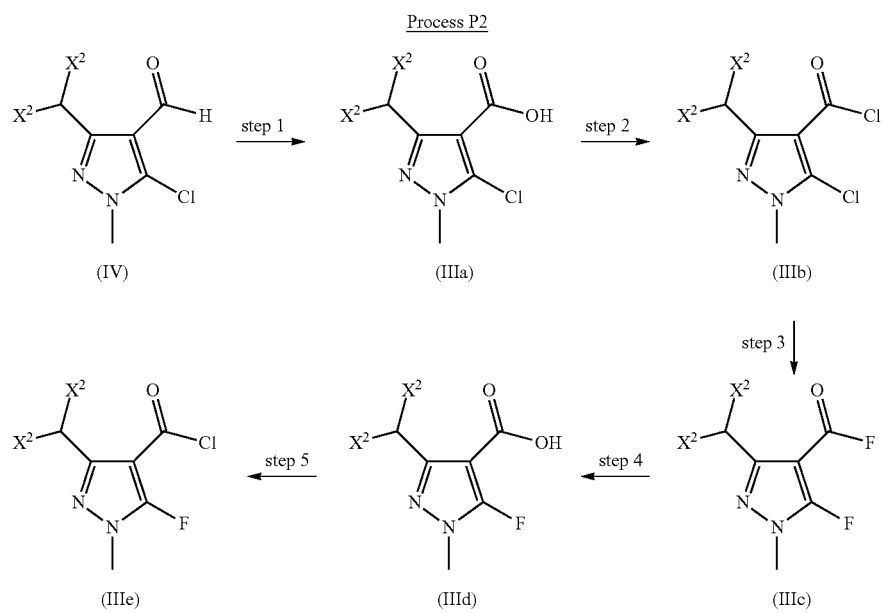

wherein $X^2$ is as herein-defined;

5-chloro-3-(difluoromethyl)-1-methyl-1H-pyrazole-4-carbaldehyde is known from WO-2004/014138 (reference example 35).

Step 1 of process P2 is performed in the presence of an oxidant, and if appropriate in the presence of a solvent.

Steps 2 and 5 of process P2 are performed in the presence of acid halide, and if appropriate in the presence of a solvent.

When carrying out steps 1 to 5 of process P2 according to the invention, the reaction temperatures can independently be varied within a relatively wide range. Generally, processes according to the invention are carried out at temperatures between 0° C. and 160° C., preferably between 10° C. and 120° C. A way to control the temperature for the processes according to the invention is to use the micro-wave technology.

Steps 1 to 5 of process P2 according to the invention are generally independently carried out under atmospheric pressure. However, in each case, it is also possible to operate under elevated or reduced pressure.

When carrying out step 1 of process P2 according to the invention, generally one mole or excess amount of the oxidant is employed per mole of aldehyde of formula (IV). It is also possible to employ the reaction components in other ratios.

When carrying out steps 2 and 5 of process P2 according to the invention, generally one mole or excess amount of the acid halides is employed per mole of acid of formula (IIIa) or (IIId). It is also possible to employ the reaction components in other ratios.

When carrying out steps 3 of process P2 according to the invention, generally one mole or excess amount of fluorinating agent is employed per mole of acid chloride (IIIb). It is also possible to employ the reaction components in other ratios.

When carrying out steps 4 of process P2 according to the invention, generally one mole or excess amount of acid or base is employed per mole of acid fluoride (IIIc). It is also possible to employ the reaction components in other ratios.

According to a further aspect of the invention, there is provided a process P3 for the preparation of a compound of formula (I) wherein T represents S, starting from a compound of formula (I) wherein T represents O and illustrated according to the following reaction scheme:

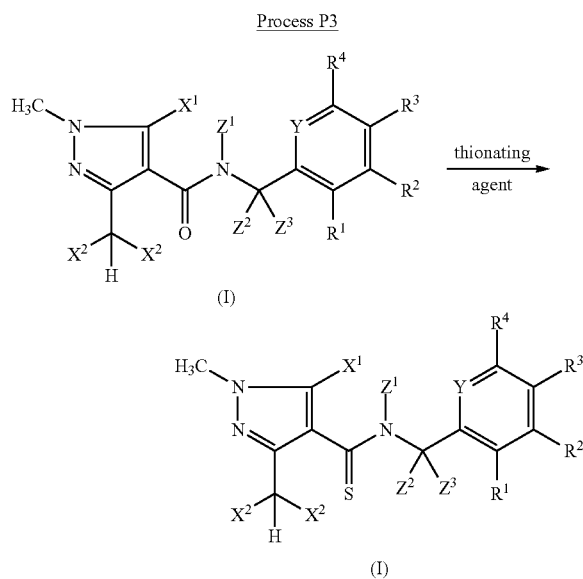

wherein $X^1$, $X^2$, $Z^1$, $Z^2$, $Z^3$, Y, $R^1$, $R^2$, $R^3$ and $R^4$ are as herein defined, in the optional presence of a catalytic or stoichiometric or excess amount, quantity of a base such as an inorganic and organic base. Preference is given to using alkali metal carbonates, such as sodium carbonate, potassium carbonate, potassium bicarbonate, sodium bicarbonate; heterocyclic aromatic bases, such as pyridine, picoline, lutidine, collidine; and also tertiary amines, such as trimethylamine, triethylamine, tributylamine, N,N-dimethylaniline, N,N-dimethylaminopyridine or N-methyl-piperidine.

Process P3 according to the invention is performed in the presence of a thionating agent.

Starting amide derivatives of formula (I) can be prepared according to process P1.

Suitable thionating agents for carrying out process P3 according to the invention can be sulfur (S), sulfhydric acid (H2S), sodium sulfide (Na2S), sodium hydrosulfide (NaHS), boron trisulfide (B2S3), bis(diethylaluminium) sulfide ((AlEt2)2S), ammonium sulfide ((NH4)2S), phosphorous pentasulfide (P2S5), Lawesson's reagent (2,4-bis(4-methoxyphenyl)-1,2,3,4-dithiadiphos-phetane 2,4-disulfide) or a polymer-supported thionating reagent such as described in Journal of the Chemical Society, Perkin 1 (2001), 358.

Work-up is carried out by customary methods. Generally, the reaction mixture is treated with water and the organic phase is separated off and, after drying, concentrated under reduced pressure. If appropriate, the remaining residue can, be freed by customary methods, such as chromatography, recrystallization or distillation, from any impurities that may still be present.

The compound according to the present invention can be prepared according to the general processes of preparation described above. It will nevertheless be understood that, on the basis of his general knowledge and of available publications, the skilled worker will be able to adapt this method according to the specifics of each of the compounds, which it is desired to synthesize.

In a further aspect, the present invention also relates to a fungicide composition comprising an effective and non-phytotoxic amount of an active compound of formula (I).

The expression "effective and non-phytotoxic amount" means an amount of composition according to the invention that is sufficient to control or destroy the fungi present or liable to appear on the cropsand that does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials that are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic, organic or inorganic compound with that the active compound of formula (I) is combined or associated to make it easier to apply, notably to the parts of the plant. This support is thus generally inert and should be agriculturally acceptable. The support can be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulfonic acid salts, phenolsulfonic or naphthalenesulfonic acid salts, polycondensates of ethylene oxide with fatty alcohols or with fatty acids or with fatty amines, substituted phenols (in particular alkylphenols or arylphenols), salts of sulfosuccinic acid esters, taurine derivatives (in particular alkyl taurates), phosphoric esters of polyoxyethylated alcohols or phenols, fatty acid esters of polyolsand derivatives of the above compounds containing sulfate, sulfonate and phosphate functions. The presence of at least one surfactant is generally essential when the active compound and/or the inert support are water-insoluble and when the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, that complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions that are ready to be applied to the plant or seed to be treated by means of a suitable device, such as a spraying or dusting device, but also concentrated commercial compositions that must be diluted before application to the crop.

The compounds according to the invention can also be mixed with one or more insecticide, fungicide, bactericide, attractant, acaricide or pheromone active substance or other compounds with biological activity. The mixtures thus obtained have normally a broadened spectrum of activity. The mixtures with other fungicide compounds are particularly advantageous.

Examples of suitable fungicide mixing partners can be selected in the following lists:

(1) Inhibitors of the ergosterol biosynthesis, for example (1.1) aldimorph (1704-28-5), (1.2) azaconazole (60207-31-0), (1.3) bitertanol (55179-31-2), (1.4) bromuconazole (116255-48-2), (1.5) cyproconazole (113096-99-4), (1.6) diclobutrazole (75736-33-3), (1.7) difenoconazole (119446-68-3), (1.8) diniconazole (83657-24-3), (1.9) diniconazole-M (83657-18-5), (1.10) dodemorph (1593-77-7), (1.11) dodemorph acetate (31717-87-0), (1.12) epoxiconazole (106325-08-0), (1.13) etaconazole (60207-93-4), (1.14) fenarimol (60168-88-9), (1.15) fenbuconazole (114369-43-6), (1.16) fenhexamid (126833-17-8), (1.17) fenpropidin (67306-00-7), (1.18) fenpropimorph (67306-03-0), (1.19) fluquinconazole (136426-54-5), (1.20) flurprimidol (56425-91-3), (1.21) flusilazole (85509-19-9), (1.22) flutriafol (76674-21-0), (1.23) furconazole (112839-33-5), (1.24) furconazole-cis (112839-32-4), (1.25) hexaconazole (79983-71-4), (1.26) imazalil (60534-80-7), (1.27) imazalil sulfate (58594-72-2), (1.28) imibenconazole (86598-92-7), (1.29) ipconazole (125225-28-7), (1.30) metconazole (125116-23-6), (1.31) myclobutanil (88671-89-0), (1.32) naftifine (65472-88-0), (1.33) nuarimol (63284-71-9), (1.34) oxpoconazole (174212-12-5), (1.35) paclobutrazol (76738-62-0), (1.36) pefurazoate (101903-30-4), (1.37) penconazole (66246-88-6), (1.38) piperalin (3478-94-2), (1.39) prochloraz (67747-09-5), (1.40) propiconazole (60207-90-1), (1.41) prothioconazole (178928-70-6), (1.42) pyributicarb (88678-67-5), (1.43) pyrifenox (88283-41-4), (1.44) quinconazole (103970-75-8), (1.45) simeconazole (149508-90-7), (1.46) spiroxamine (118134-30-8), (1.47) tebuconazole (107534-96-3), (1.48) terbinafine (91161-71-6), (1.49) tetraconazole (112281-77-3), (1.50) triadimefon (43121-43-3), (1.51) triadimenol (89482-17-7), (1.52) tridemorph (81412-43-3), (1.53) triflumizole (68694-11-1), (1.54) triforine (26644-46-2), (1.55) triticonazole (131983-72-7), (1.56) uniconazole (83657-22-1), (1.57) uniconazole-p (83657-17-4), (1.58) viniconazole (77174-66-4), (1.59) voriconazole (137234-62-9), (1.60) 1-(4-chlorophenyl)-2-(1H-1,2,4-triazol-1-yl)cycloheptanol (129586-32-9), (1.61) methyl 1-(2,2-dimethyl-2,3-dihydro-1H-inden-1-yl)-1H-imidazole-5-carboxylate (110323-95-0), (1.62) N'-{5-(difluoromethyl)-2-methyl-4-[3-(trimethylsilyl)propox]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide and (1.64) O-[1-(4-methoxyphenoxy)-3,3-dimethylbutan-2-yl]1H-imidazole-1-carbothioate (111226-71-2).

(2) inhibitors of the respiratory chain at complex I or II, for example (2.1) bixafen (581809-46-3), (2.2) boscalid (188425-85-6), (2.3) carboxin (5234-68-4), (2.4) diflumetorim (130339-07-0), (2.5) fenfuram (24691-80-5), (2.6) fluopyram (658066-35-4), (2.7) flutolanil (66332-96-5), (2.8) fluxapyroxad (907204-31-3), (2.9) furametpyr (123572-88-3), (2.10) furmecyclox (60568-05-0), (2.11) isopyrazam (mixture of syn-epimeric racemate 1RS,4SR,9RS and anti-epimeric racemate 1RS,4SR,9SR) (881685-58-1), (2.12) isopyrazam (anti-epimeric racemate 1 RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil (55814-41-0), (2.19) oxycarboxin (5259-88-1), (2.20) penflufen (494793-67-8), (2.21) penthiopyrad (183675-82-3), (2.22) sedaxane (874967-67-6), (2.23) thifluzamide (130000-40-7), (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide (1092400-95-7) (WO 2008148570), (2.28) 5,8-difluoro-N-[2-(2-fluoro-4-{[4-(trifluoromethyl)pyridin-2-yl]oxy}phenyl)ethyl]quinazolin-4-amine (1210070-84-0) (WO2010025451), (2.29) N-[9-(dichloromethylene)-1,2,3,4-tetrahydro-1,4-methanonaphthalen-5-yl]-3-(difluoromethyl)-1-methyl-1H-pyrazole-4-carboxamide, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide and (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide.

(3) inhibitors of the respiratory chain at complex III, for example (3.1) ametoctradin (865318-97-4), (3.2) amisulbrom (348635-87-0), (3.3) azoxystrobin (131860-33-8), (3.4) cyazofamid (120116-88-3), (3.5) coumethoxystrobin (850881-30-0), (3.6) coumoxystrobin (850881-70-8), (3.7) dimoxystrobin (141600-52-4), (3.8) enestroburin (238410-

11-2) (WO 2004/058723), (3.9) famoxadone (131807-57-3) (WO 2004/058723), (3.10) fenamidone (161326-34-7) (WO 2004/058723), (3.11) fenoxystrobin (918162-02-4), (3.12) fluoxastrobin (361377-29-9) (WO 2004/058723), (3.13) kresoxim-methyl (143390-89-0) (WO 2004/058723), (3.14) metominostrobin (133408-50-1) (WO 2004/058723), (3.15) orysastrobin (189892-69-1) (WO 2004/058723), (3.16) picoxystrobin (117428-22-5) (WO 2004/058723), (3.17) pyraclostrobin (175013-18-0) (WO 2004/058723), (3.18) pyrametostrobin (915410-70-7) (WO 2004/058723), (3.19) pyraoxystrobin (862588-11-2) (WO 2004/058723), (3.20) pyribencarb (799247-52-2) (WO 2004/058723), (3.21) triclopyricarb (902760-40-1), (3.22) trifloxystrobin (141517-21-7) (WO 2004/058723), (3.23) (2E)-2-(2-{[6-(3-chloro-2-methylphenoxy)-5-fluoropyrimidin-4-yl]oxy}phenyl)-2-(methoxyimino)-N-methylethanamide (WO 2004/058723), (3.24) (2E)-2-(methoxyimino)-N-methyl-2-(2-{[({(1E)-1-[3-(trifluoromethyl)phenyl]ethylidene}amino)oxy]methyl}phenyl)ethanamide (WO 2004/058723), (3.25) (2E)-2-(methoxyimino)-N-methyl-2-{2-[(E)-({1-[3-(trifluoromethyl)phenyl]ethoxy}imino)methyl]phenyl}ethanamide (158169-73-4), (3.26) (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide (326896-28-0), (3.27) (2E)-2-{2-[({[(2E,3E)-4-(2,6-dichlorophenyl)but-3-en-2-ylidene]amino}oxy)methyl]phenyl}-2-(methoxyimino)-N-methylethanamide, (3.28) 2-chloro-N-(1,1,3-trimethyl-2,3-dihydro-1H-inden-4-yl)pyridine-3-carboxamide (119899-14-8), (3.29) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.30) methyl (2E)-2-{2-[({cyclopropyl[(4-methoxyphenyl)imino]methyl}sulfanyl)methyl]phenyl}-3-methoxyprop-2-enoate (149601-03-6), (3.31) N-(3-ethyl-3,5,5-trimethylcyclohexyl)-3-(formylamino)-2-hydroxybenzamide (226551-21-9), (3.32) 2-{2-[(2,5-dimethylphenoxy)methyl]phenyl}-2-methoxy-N-methylacetamide (173662-97-0) and (3.33) (2R)-2-{2-[(2,5-dimethylphenoxy)methyl]phenyl}-2-methoxy-N-methylacetamide (394657-24-0).

(4) Inhibitors of the mitosis and cell division, for example (4.1) benomyl (17804-35-2), (4.2) carbendazim (10605-21-7), (4.3) chlorfenazole (3574-96-7), (4.4) diethofencarb (87130-20-9), (4.5) ethaboxam (162650-77-3), (4.6) fluopicolide (239110-15-7), (4.7) fuberidazole (3878-19-1), (4.8) pencycuron (66063-05-6), (4.9) thiabendazole (148-79-8), (4.10) thiophanate-methyl (23564-05-8), (4.11) thiophanate (23564-06-9), (4.12) zoxamide (156052-68-5), (4.13) 5-chloro-7-(4-methylpiperidin-1-yl)-6-(2,4,6-trifluorophenyl)[1,2,4]triazolo[1,5-a]pyrimidine (214706-53-3) and (4.14) 3-chloro-5-(6-chloropyridin-3-yl)-6-methyl-4-(2,4,6-trifluorophenyl)pyridazine (1002756-87-7).

(5) Compounds capable to have a multisite action, like for example (5.1) bordeaux mixture (8011-63-0), (5.2) captafol (2425-06-1), (5.3) captan (133-06-2) (WO 02/12172), (5.4) chlorothalonil (1897-45-6), (5.5) copper hydroxide (20427-59-2), (5.6) copper naphthenate (1338-02-9), (5.7) copper oxide (1317-39-1), (5.8) copper oxychloride (1332-40-7), (5.9) copper(2+) sulfate (7758-98-7), (5.10) dichlofluanid (1085-98-9), (5.11) dithianon (3347-22-6), (5.12) dodine (2439-10-3), (5.13) dodine free base, (5.14) ferbam (14484-64-1), (5.15) fluorofolpet (719-96-0), (5.16) folpet (133-07-3), (5.17) guazatine (108173-90-6), (5.18) guazatine acetate, (5.19) iminoctadine (13516-27-3), (5.20) iminoctadine albesilate (169202-06-6), (5.21) iminoctadine triacetate (57520-17-9), (5.22) mancopper (53988-93-5), (5.23) mancozeb (8018-01-7), (5.24) maneb (12427-38-2), (5.25) metiram (9006-42-2), (5.26) metiram zinc (9006-42-2), (5.27) oxine-copper (10380-28-6), (5.28) propamidine (104-32-5), (5.29) propineb (12071-83-9), (5.30) sulfur and sulfur preparations including calcium polysulfide (7704-34-9), (5.31) thiram (137-26-8), (5.32) tolylfluanid (731-27-1), (5.33) zineb (12122-67-7) and (5.34) ziram (137-30-4).

(6) Compounds capable to induce a host defence, for example (6.1) acibenzolar-5-methyl (135158-54-2), (6.2) isotianil (224049-04-1), (6.3) probenazole (27605-76-1) and (6.4) tiadinil (223580-51-6).

(7) Inhibitors of the amino acid and/or protein biosynthesis, for example (7.1) andoprim (23951-85-1), (7.2) blasticidin-S (2079-00-7), (7.3) cyprodinil (121552-61-2), (7.4) kasugamycin (6980-18-3), (7.5) kasugamycin hydrochloride hydrate (19408-46-9), (7.6) mepanipyrim (110235-47-7), (7.7) pyrimethanil (53112-28-0) and (7.8) 3-(5-fluoro-3,3,4,4-tetramethyl-3,4-dihydroisoquinolin-1-yl)quinoline (861647-32-7) (WO2005070917).

(8) Inhibitors of the ATP production, for example (8.1) fentin acetate (900-95-8), (8.2) fentin chloride (639-58-7), (8.3) fentin hydroxide (76-87-9) and (8.4) silthiofam (175217-20-6).

(9) Inhibitors of the cell wall synthesis, for example (9.1) benthiavalicarb (177406-68-7), (9.2) dimethomorph (110488-70-5), (9.3) flumorph (211867-47-9), (9.4) iprovalicarb (140923-17-7), (9.5) mandipropamid (374726-62-2), (9.6) polyoxins (11113-80-7), (9.7) polyoxorim (22976-86-9), (9.8) validamycin A (37248-47-8) and (9.9) valifenalate (283159-94-4; 283159-90-0).

(10) Inhibitors of the lipid and membrane synthesis, for example (10.1) biphenyl (92-52-4), (10.2) chloroneb (2675-77-6), (10.3) dicloran (99-30-9), (10.4) edifenphos (17109-49-8), (10.5) etridiazole (2593-15-9), (10.6) iodocarb (55406-53-6), (10.7) iprobenfos (26087-47-8), (10.8) isoprothiolane (50512-35-1), (10.9) propamocarb (25606-41-1), (10.10) propamocarb hydrochloride (25606-41-1), (10.11) prothiocarb (19622-08-3), (10.12) pyrazophos (13457-18-6), (10.13) quintozene (82-68-8), (10.14) tecnazene (117-18-0) and (10.15) tolclofos-methyl (57018-04-9).

(11) Inhibitors of the melanine biosynthesis, for example (11.1) carpropamid (104030-54-8), (11.2) diclocymet (139920-32-4), (11.3) fenoxanil (115852-48-7), (11.4) phthalide (27355-22-2), (11.5) pyroquilon (57369-32-1), (11.6) tricyclazole (41814-78-2) and (11.7) 2,2,2-trifluoroethyl {3-methyl-1-[(4-methylbenzoyl)amino]butan-2-yl}carbamate (851524-22-6) (WO2005042474).

(12) Inhibitors of the nucleic acid synthesis, for example (12.1) benalaxyl (71626-11-4), (12.2) benalaxyl-M (kiralaxyl) (98243-83-5), (12.3) bupirimate (41483-43-6), (12.4) clozylacon (67932-85-8), (12.5) dimethirimol (5221-53-4), (12.6) ethirimol (23947-60-6), (12.7) furalaxyl (57646-30-7), (12.8) hymexazol (10004-44-1), (12.9) metalaxyl (57837-19-1), (12.10) metalaxyl-M (mefenoxam) (70630-17-0), (12.11) ofurace (58810-48-3), (12.12) oxadixyl (77732-09-3) and (12.13) oxolinic acid (14698-29-4).

(13) Inhibitors of the signal transduction, for example (13.1) chlozolinate (84332-86-5), (13.2) fenpiclonil (74738-17-3), (13.3) fludioxonil (131341-86-1), (13.4) iprodione (36734-19-7), (13.5) procymidone (32809-16-8), (13.6) quinoxyfen (124495-18-7) and (13.7) vinclozolin (50471-44-8).

(14) Compounds capable to act as an uncoupler, for example (14.1) binapacryl (485-31-4), (14.2) dinocap (131-72-6), (14.3) ferimzone (89269-64-7), (14.4) fluazinam (79622-59-6) and (14.5) meptyldinocap (131-72-6).

(15) Further compounds, for example (15.1) benthiazole (21564-17-0), (15.2) bethoxazin (163269-30-5), (15.3) capsimycin (70694-08-5), (15.4) carvone (99-49-0), (15.5)

chinomethionat (2439-01-2), (15.6) pyriofenone (chlazafenone) (688046-61-9), (15.7) cufraneb (11096-18-7), (15.8) cyflufenamid (180409-60-3), (15.9) cymoxanil (57966-95-7), (15.10) cyprosulfamide (221667-31-8), (15.11) dazomet (533-74-4), (15.12) debacarb (62732-91-6), (15.13) dichlorophen (97-23-4), (15.14) diclomezine (62865-36-5), (15.15) difenzoquat (49866-87-7), (15.16) difenzoquat methylsulfate (43222-48-6), (15.17) diphenylamine (122-39-4), (15.18) ecomate, (15.19) fenpyrazamine (473798-59-3), (15.20) flumetover (154025-04-4), (15.21) fluoroimide (41205-21-4), (15.22) flusulfamide (106917-52-6), (15.23) flutianil (304900-25-2), (15.24) fosetyl-aluminium (39148-24-8), (15.25) fosetyl-calcium, (15.26) fosetyl-sodium (39148-16-8), (15.27) hexachlorobenzene (118-74-1), (15.28) irumamycin (81604-73-1), (15.29) methasulfocarb (66952-49-6), (15.30) methyl isothiocyanate (556-61-6), (15.31) metrafenone (220899-03-6), (15.32) mildiomycin (67527-71-3), (15.33) natamycin (7681-93-8), (15.34) nickel dimethyldithiocarbamate (15521-65-0), (15.35) nitrothal-isopropyl (10552-74-6), (15.36) octhilinone (26530-20-1), (15.37) oxamocarb (917242-12-7), (15.38) oxyfenthiin (34407-87-9), (15.39) pentachlorophenol and salts (87-86-5), (15.40) phenothrin, (15.41) phosphorous acid and its salts (13598-36-2), (15.42) propamocarb-fosetylate, (15.43) propanosine-sodium (88498-02-6), (15.44) proquinazid (189278-12-4), (15.45) pyrimorph (868390-90-3), (15.45e) (2E)-3-(4-tert-butylphenyl)-3-(2-chloropyridin-4-yl)-1-(morpholin-4-yl)prop-2-en-1-one (1231776-28-5), (15.45z) (2Z)-3-(4-tert-butylphenyl)-3-(2-chloropyridin-4-yl)-1-(morpholin-4-yl)prop-2-en-1-one (1231776-29-6), (15.46) pyrrolnitrine (1018-71-9) (EP-A 1 559 320), (15.47) tebufloquin (376645-78-2), (15.48) tecloftalam (76280-91-6), (15.49) tolnifanide (304911-98-6), (15.50) triazoxide (72459-58-6), (15.51) trichlamide (70193-21-4), (15.52) zarilamid (84527-51-5), (15.53) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate (517875-34-2) (WO2003035617), (15.54) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-79-6) (WO 2008013622), (15.55) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003319-80-9) (WO 2008013622), (15.56) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone (1003318-67-9) (WO 2008013622), (15.57) 1-(4-methoxyphenoxy)-3,3-dimethylbutan-2-yl1H-imidazole-1-carboxylate (111227-17-9), (15.58) 2,3,5,6-tetrachloro-4-(methylsulfonyl)pyridine (13108-52-6), (15.59) 2,3-dibutyl-6-chlorothieno[2,3-d]pyrimidin-4(3H)-one (221451-58-7), (15.60) 2,6-dimethyl-1H,5H-[1,4]dithiino[2,3-c:5,6-c'] dipyrrole-1,3,5,7(2H,6H)-tetrone, (15.61) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone (1003316-53-7) (WO 2008013622), (15.62) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone (1003316-54-8) (WO 2008013622), (15.63) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone (1003316-51-5) (WO 2008013622), (15.64) 2-butoxy-6-iodo-3-propyl-4H-chromen-4-one, (15.65) 2-chloro-5-[2-chloro-1-(2,6-difluoro-4-methoxyphenyl)-4-methyl-1H-imidazol-5-yl]pyridine, (15.66) 2-phenylphenol and salts (90-43-7), (15.67) 3-(4,4,5-trifluoro-3,3-dimethyl-3,4-dihydroisoquinolin-1-yl)quinoline (861647-85-0) (WO2005070917), (15.68) 3,4,5-trichloropyridine-2,6-dicarbonitrile (17824-85-0), (15.69) 3-[5-(4-chlorophenyl)-2,3-dimethyl-1,2-oxazolidin-3-yl]pyridine, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulfonohydrazide (134-31-6), (15.74) 5-fluoro-2-[(4-fluorobenzyl)oxy]pyrimidin-4-amine (1174376-11-4) (WO2009094442), (15.75) 5-fluoro-2-[(4-methylbenzyl)oxy]pyrimidin-4-amine (1174376-25-0) (WO2009094442), (15.76) 5-methyl-6-octyl[1,2,4]triazolo[1,5-a]pyrimidin-7-amine, (15.77) ethyl (2Z)-3-amino-2-cyano-3-phenylprop-2-enoate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl] propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloropyridine-3-carboxamide, (15.82) N-[1-(5-bromo-3-chloropyridin-2-yl)ethyl]-2,4-dichloropyridine-3-carboxamide, (15.83) N-[1-(5-bromo-3-chloropyridin-2-yl)ethyl]-2-fluoro-4-iodopyridine-3-carboxamide, (15.84) N-{(E)-[(cyclopropylmethoxy)imino][6-(difluoromethoxy)-2,3-difluorophenyl]methyl}-2-phenylacetamide (221201-92-9), (15.85) N-{(Z)-[(cyclopropylmethoxy)imino][6-(difluoromethoxy)-2,3-difluorophenyl]methyl}-2-phenylacetamide (221201-92-9), (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide (922514-49-6) (WO 2007014290), (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide (922514-07-6) (WO 2007014290), (15.89) N-methyl-2-(1-{[5-methyl-3-(trifluoromethyl)-1H-pyrazol-1-yl] acetyl}piperidin-4-yl)-N-[(1S)-1,2,3,4-tetrahydronaphthalen-1-yl]-1,3-thiazole-4-carboxamide (922514-48-5) (WO 2007014290), (15.90) pentyl {6-[({[(1-methyl-1H-tetrazol-5-yl)(phenyl)methylidene]amino}oxy) methyl]pyridin-2-yl}carbamate, (15.91) phenazine-1-carboxylic acid, (15.92) quinolin-8-ol (134-31-6), (15.93) quinolin-8-ol sulfate (2:1) (134-31-6) and (15.94) tert-butyl {6[({[(1-methyl-1H-tetrazol-5-yl)(phenyl)methylene] amino}oxy)methyl]pyridin-2-yl}carbamate.

(16) Further compounds, for example (16.1) 1-methyl-3-(trifluoromethyl)-N-[2'-(trifluoromethyl)biphenyl-2-yl]-1H-pyrazole-4-carboxamide, (16.2) N-(4'-chlorobiphenyl-2-yl)-3-(difluoromethyl)-1-methyl-1H-pyrazole-4-carboxamide, (16.3) N-(2',4'-dichlorobiphenyl-2-yl)-3-(difluoromethyl)-1-methyl-1H-pyrazole-4-carboxamide, (16.4) 3-(difluoromethyl)-1-methyl-N-[4'-(trifluoromethyl)biphenyl-2-yl]-1H-pyrazole-4-carboxamide, (16.5) N-(2',5'-difluorobiphenyl-2-yl)-1-methyl-3-(trifluoromethyl)-1H-pyrazole-4-carboxamide, (16.6) 3-(difluoromethyl)-1-methyl-N-[4'-(prop-1-yn-1-yl)biphenyl-2-yl]-1H-pyrazole-4-carboxamide (known from WO 2004/058723), (16.7) 5-fluoro-1,3-dimethyl-N-[4'-(prop-1-yn-1-yl)biphenyl-2-yl]-1H-pyrazole-4-carboxamide (known from WO 2004/058723), (16.8) 2-chloro-N-[4'-(prop-1-yn-1-yl)biphenyl-2-yl]pyridine-3-carboxamide (known from WO 2004/058723), (16.9) 3-(difluoromethyl)-N-[4'-(3,3-dimethylbut-1-yn-1-yl)

biphenyl-2-yl]-1-methyl-1H-pyrazole-4-carboxamide (known from WO 2004/058723), (16.10) N-[4'-(3,3-dimethylbut-1-yn-1-yl)biphenyl-2-yl]-5-fluoro-1,3-dimethyl-1H-pyrazole-4-carboxamide (known from WO 2004/058723), (16.11) 3-(difluoromethyl)-N-(4'-ethynylbiphenyl-2-yl)-1-methyl-1H-pyrazole-4-carboxamide (known from WO 2004/058723), (16.12) N-(4'-ethynylbiphenyl-2-yl)-5-fluoro-1,3-dimethyl-1H-pyrazole-4-carboxamide (known from WO 2004/058723), (16.13) 2-chloro-N-(4'-ethynylbiphenyl-2-yl)pyridine-3-carboxamide (known from WO 2004/058723), (16.14) 2-chloro-N-[4'-(3,3-dimethylbut-1-yn-1-yl)biphenyl-2-yl]pyridine-3-carboxamide (known from WO 2004/058723), (16.15) 4-(difluoromethyl)-2-methyl-N-[4'-(trifluoromethyl)biphenyl-2-yl]-1,3-thiazole-5-carboxamide (known from WO 2004/058723), (16.16) 5-fluoro-N-[4'-(3-hydroxy-3-methylbut-1-yn-1-yl)biphenyl-2-yl]-1,3-dimethyl-1H-pyrazole-4-carboxamide (known from WO 2004/058723), (16.17) 2-chloro-N-[4'-(3-hydroxy-3-methylbut-1-yn-1-yl)biphenyl-2-yl]pyridine-3-carboxamide (known from WO 2004/058723), (16.18) 3-(difluoromethyl)-N-[4'-(3-methoxy-3-methylbut-1-yn-1-yl)biphenyl-2-yl]-1-methyl-1H-pyrazole-4-carboxamide (known from WO 2004/058723), (16.19) 5-fluoro-N-[4'-(3-methoxy-3-methylbut-1-yn-1-yl)biphenyl-2-yl]-1,3-dimethyl-1H-pyrazole-4-carboxamide (known from WO 2004/058723), (16.20) 2-chloro-N-[4'-(3-methoxy-3-methylbut-1-yn-1-yl)biphenyl-2-yl]pyridine-3-carboxamide (known from WO 2004/058723), (16.21) (5-bromo-2-methoxy-4-methylpyridin-3-yl)(2,3,4-trimethoxy-6-methylphenyl)methanone (known from EP-A 1 559 320), (16.22) N-[2-(4-{[3-(4-chlorophenyl)prop-2-yn-1-yl]oxy}-3-methoxyphenyl)ethyl]-N2-(methylsulfonyl)valinamide (220706-93-4), (16.23) 4-oxo-4-[(2-phenylethyl)amino]butanoic acid and (16.24) but-3-yn-1-yl{6-[({[(Z)-(1-methyl-1H-tetrazol-5-yl)(phenyl)methylene]amino}oxy)methyl]pyridin-2-yl}carbamate.

All named mixing partners of the classes (1) to (16) can, if their functional groups enable this, optionally form salts with suitable bases or acids.

Examples of suitable bactericides, insecticides, acaricides or nematicides mixing partners can be selected in the following lists:

Bactericides:
Bronopol, dichlorophen, nitrapyrin, nickel dimethyl dithiocarbamate, kasugamycin, octhilinone, furan-carboxylic acid, oxytetracyclin, probenazole, streptomycin, tecloftalam, copper sulfate and other copper preparations.

Insecticides/Acaricides/Nematicides:
(1) Acetylcholinesterase (AChE) inhibitors, for example
carbamates, e.g. Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC, and Xylylcarb; or
organophosphates, e.g. Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-5-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl) salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Trichlorfon, and Vamidothion.

(2) GABA-gated chloride channel antagonists, for example
cyclodiene organochlorines, e.g. Chlordane and Endosulfan; or
phenylpyrazoles (fiproles), e.g. Ethiprole and Fipronil.

(3) Sodium channel modulators/voltage-dependent sodium channel blockers, for example
pyrethroids, e.g. Acrinathrin, Allethrin, d-cis-trans Allethrin, d-trans Allethrin, Bifenthrin, Bioallethrin, Bioallethrin 5-cyclopentenyl isomer, Bioresmethrin, Cycloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin [(1R)-trans isomers], Deltamethrin, Empenthrin [(EZ)-(1R) isomers), Esfenvalerate, Etofenprox, Fenpropathrin, Fenvalerate, Flucythrinate, Flumethrin, tau-Fluvalinate, Halfenprox, Imiprothrin, Kadethrin, Permethrin, Phenothrin [(1R)-trans isomer), Prallethrin, Pyrethrine (pyrethrum), Resmethrin, Silafluofen, Tefluthrin, Tetramethrin, Tetramethrin [(1R) isomers)], Tralomethrin, and Transfluthrin; or
DDT; or Methoxychlor.

(4) Nicotinic acetylcholine receptor (nAChR) agonists, for example
neonicotinoids, e.g. Acetamiprid, Clothianidin, Dinotefuran, Imidacloprid, Nitenpyram, Thiacloprid, and Thiamethoxam; or
Nicotine.

(5) Nicotinic acetylcholine receptor (nAChR) allosteric activators, for example
spinosyns, e.g. Spinetoram and Spinosad.

(6) Chloride channel activators, for example
avermectins/milbemycins, e.g. Abamectin, Emamectin benzoate, Lepimectin, and Milbemectin.

(7) Juvenile hormone mimics, for example
juvenile hormon analogues, e.g. Hydroprene, Kinoprene, and Methoprene; or
Fenoxycarb; or Pyriproxyfen.

(8) Miscellaneous non-specific (multi-site) inhibitors, for example
alkyl halides, e.g. Methyl bromide and other alkyl halides; or
Chloropicrin; or Sulfuryl fluoride; or Borax; or Tartar emetic.

(9) Selective homopteran feeding blockers, e.g. Pymetrozine; or Flonicamid.

(10) Mite growth inhibitors, e.g. Clofentezine, Hexythiazox, and Diflovidazin; or
Etoxazole.

(11) Microbial disruptors of insect midgut membranes, e.g. Bacillus thuringiensis subspecies israelensis, Bacillus sphaericus, Bacillus thuringiensis subspecies aizawai, Bacillus thuringiensis subspecies kurstaki, Bacillus thuringiensis subspecies tenebrionis, and BT crop proteins: Cry1Ab, Cry1Ac, Cry1Fa, Cry2Ab, mCry3A, Cry3Ab, Cry3Bb, Cry34/35Ab1.

(12) Inhibitors of mitochondria! ATP synthase, for example Diafenthiuron; or
organotin miticides, e.g. Azocyclotin, Cyhexatin, and Fenbutatin oxide; or
Propargite; or Tetradifon.

(13) Uncouplers of oxidative phoshorylation via disruption of the proton gradient, for example Chlorfenapyr, DNOC, and Sulfluramid.

(14) Nicotinic acetylcholine receptor (nAChR) channel blockers, for example Bensultap, Cartap hydrochloride, Thiocyclam, and Thiosultap-sodium.

(15) Inhibitors of chitin biosynthesis, type 0, for example Bistrifluron, Chlorfluazuron, Diflubenzuron, Flucycloxuron, Flufenoxuron, Hexaflumuron, Lufenuron, Novaluron, Noviflumuron, Teflubenzuron, and Triflumuron.

(16) Inhibitors of chitin biosynthesis, type 1, for example Buprofezin.

(17) Moulting disruptors, for example Cyromazine.

(18) Ecdysone receptor agonists, for example Chromafenozide, Halofenozide, Methoxyfenozide, and Tebufenozide.

(19) Octopamine receptor agonists, for example Amitraz.

(20) Mitochondrial complex III electron transport inhibitors, for example Hydramethylnon; or Acequinocyl; or Fluacrypyrim.

(21) Mitochondrial complex I electron transport inhibitors, for example
METI acaricides, e.g. Fenazaquin, Fenpyroximate, Pyrimidifen, Pyridaben, Tebufenpyrad, and Tolfenpyrad; or
Rotenone (Derris).

(22) Voltage-dependent sodium channel blockers, e.g. Indoxacarb; or Metaflumizone.

(23) Inhibitors of acetyl CoA carboxylase, for example tetronic and tetramic acid derivatives, e.g. Spirodiclofen, Spiromesifen, and Spirotetramat.

(24) Mitochondrial complex IV electron transport inhibitors, for example phosphines, e.g. Aluminium phosphide, Calcium phosphide, Phosphine, and Zinc phosphide; or Cyanide.

(25) Mitochondrial complex II electron transport inhibitors, for example Cyenopyrafen.

(28) Ryanodine receptor modulators, for example
diamides, e.g. Chlorantraniliprole and Flubendiamide.

Further active ingredients with unknown or uncertain mode of action, for example Amidoflumet, Azadirachtin, Benclothiaz, Benzoximate, Bifenazate, Bromopropylate, Chinomethionat, Cryolite, Cyantraniliprole (Cyazypyr), Cyflumetofen, Dicofol, Diflovidazin, Fluensulfone, Flufenerim, Flufiprole, Fluopyram, Fufenozide, Imidaclothiz, Iprodione, Meperfluthrin, Pyridalyl, Pyrifluquinazon, Tetramethylfluthrin, and iodomethane; furthermore products based on *Bacillus firmus* (including but not limited to strain CNCM I-1582, such as, for example, VOTiVO™, BioNem) or one of the following known active compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934), 4-{[(6-bromopyridin-3-yl)methyl](2-fluoroethyl)amino}furan-2(5H)-one (known from WO2007/115644), 4-{[(6-fluoropyridin-3-yl)methyl](2,2-difluoroethyl)amino}furan-2(5H)-one (known from WO2007/115644), 4-{[(2-chloro-1,3-thiazol-5-yl)methyl](2-fluoroethyl)amino}furan-2(5H)-one (known from WO2007/115644), 4-{[(6-chlorpyridin-3-yl)methyl](2-fluoroethyl)amino}furan-2(5H)-one (known from WO2007/115644), Flupyradifurone, 4-{[(6-chlor-5-fluoropyridin-3-yl)methyl](methyl)amino}furan-2(5H)-one (known from WO2007/115643), 4-{[(5,6-dichloropyridin-3-yl)methyl](2-fluoroethyl)amino}furan-2(5H)-one (known from WO2007/115646), 4-{[(6-chloro-5-fluoropyridin-3-yl)methyl](cyclopropyl)amino}furan-2(5H)-one (known from WO2007/115643), 4-{[(6-chloropyridin-3-yl)methyl](cyclopropyl)amino}furan-2(5H)-one (known from EP-A-0 539 588), 4-{[(6-chlorpyridin-3-yl)methyl](methyl)amino}furan-2(5H)-one (known from EP-A-0 539 588), {[1-(6-chloropyridin-3-yl)ethyl](methyl)oxido-$\lambda^4$-sulfanylidene}cyanamide (known from WO2007/149134) and its diastereomers {[(1R)-1-(6-chloropyridin-3-yl)ethyl]methyl)oxido-$\lambda^4$-sulfanylidene}cyanamide (A) and {[(1S)-1-(6-chloropyridin-3-yl)ethyl]methyl)oxido-$\lambda^4$-sulfanylidene}cyanamide (B) (also known from WO2007/149134) as well as Sulfoxaflor and its diastereomers [(R)-methyl(oxido){(1R)-1-[6-(trifluoromethyl)pyridin-3-yl]ethyl}-$\lambda^4$-sulfanylidene]cyanamide (A1) and [(S)-methyl(oxido){(1S)-1-[6-(trifluoromethyl)pyridin-3-yl]ethyl}-$\lambda^4$-sulfanylidene]cyanamide (A2), referred to as group of diastereomers A (known from WO2010/074747, WO2010/074751), [(R)-methyl(oxido){(1S)-1-[6-(trifluoromethyl)pyridin-3-yl]ethyl}-$\lambda^4$-sulfanylidene]cyanamide (B1) and [(S)-methyl(oxido){(1R)-1-[6-(trifluoromethyl)pyridin-3-yl]ethyl}-$\lambda^4$-sulfanylidene]cyanamide (B2), referred to as group of diastereomers B (also known from WO2010/074747, WO2010/074751), and 11-(4-chloro-2,6-dimethylphenyl)-12-hydroxy-1,4-dioxa-9-azadispiro[4.2.4.2]tetradec-11-en-10-one (known from WO2006/089633), 3-(4'-fluoro-2,4-dimethylbiphenyl-3-yl)-4-hydroxy-8-oxa-1-azaspiro[4.5]dec-3-en-2-one (known from WO2008/067911), 1-{2-fluoro-4-methyl-5-[(2,2,2-trifluorethyl)sulfinyl]phenyl}-3-(trifluoromethyl)-1H-1,2,4-triazol-5-amine (known from WO2006/043635), [(3S,4aR,12R,12aS,12bS)-3-[(cyclopropylcarbonyl)oxy]-6,12-dihydroxy-4,12b-dimethyl-11-oxo-9-(pyridin-3-yl)-1,3,4,4a,5,6,6a,12,12a,12b-decahydro-2H,11H-benzo[f]pyrano[4,3-b]chromen-4-yl]methyl cyclopropanecarboxylate (known from WO2008/066153), 2-cyano-3-(difluoromethoxy)-N,N-dimethylbenzenesulfonamide (known from WO2006/056433), 2-cyano-3-(difluoromethoxy)-N-methylbenzenesulfonamide (known from WO2006/100288), 2-cyano-3-(difluoromethoxy)-N-ethylbenzenesulfonamide (known from WO2005/035486), 4-(difluoromethoxy)-N-ethyl-N-methyl-1,2-benzothiazol-3-amine 1,1-dioxide (known from WO2007/057407), N-[1-(2,3-dimethylphenyl)-2-(3,5-dimethylphenyl)ethyl]-4,5-dihydro-1,3-thiazol-2-amine (known from WO2008/104503), {1'-[(2E)-3-(4-chlorophenyl)prop-2-en-1-yl]-5-fluorospiro[indole-3,4'-piperidin]-1(2H)-yl}(2-chloropyridin-4-yl)methanone (known from WO2003/106457), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), (2,2,3,3,4,4,5,5-octafluoropentyl)(3,3,3-trifluoropropyl)malononitrile (known from WO2005/063094), (2,2,3,3,4,4,5,5-octafluoropentyl)(3,3,4,4,4-pentafluorobutyl)malononitrile (known from WO2005/063094), 8-[2-(cyclopropylmethoxy)-4-(trifluoromethyl)phenoxy]-3-[6-(trifluoromethyl)pyridazin-3-yl]-3-azabicyclo[3.2.1]octane (known from WO2007/040280), Flometoquin, PF1364 (CAS-Reg. No. 1204776-60-2) (known from JP2010/018586), 5-[5-(3,5-dichlorophenyl)-5-(trifluoromethyl)-4,5-dihydro-1,2-oxazol-3-yl]-2-(1H-1,2,4-triazol-1-yl)benzonitrile (known from WO2007/075459), 5-[5-(2-chloropyridin-4-yl)-5-(trifluoromethyl)-4,5-dihydro-1,2-oxazol-3-yl]-2-(1H-1,2,4-triazol-1-yl)benzonitrile (known from WO2007/075459), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{[(6-chloropyridin-3-yl)methyl](cyclopropyl)amino}-1,3-oxazol-2(5H)-one, 4-{[(6-chloropyridin-3-yl)methyl](2,2-difluoroethyl)amino}-1,3-oxazol-2 (5H)-one, 4-{[(6-chloropyridin-3-yl)methyl](ethyl)amino}-1,3-oxazol-2(5H)-one, 4-{[(6-chloropyridin-3-yl)methyl](methyl)amino}-1,3-oxazol-2(5H)-one (all known from WO2010/005692), NNI-0711 (known from WO2002/096882), 1-acetyl-N-[4-(1,1,1,3,3,3-hexafluoro-2-methoxypropan-2-yl)-3-isobutylphenyl]-N-isobutyryl-3,5-dimethyl-1H-pyrazole-4-carboxamide (known from WO2002/096882), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-1,2-diethylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), (5RS,7RS;5RS,7SR)-1-(6-chloro-3-pyridylmethyl)-1,2,3,5,6,7-hexahydro-7-methyl-8-nitro-5-propoxyimidazo[1,2-a]pyridine (known from WO2007/101369), 2-{6-[2-(5-fluoropyridin-3-yl)-1,3-thiazol-5-yl]pyridin-2-yl}pyrimidine (known from WO2010/006713), 2-{6-[2-(pyridin-3-yl)-1,3-thiazol-5-yl]pyridin-2-yl}pyrimidine (known from WO2010/006713), 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide (known from WO2010/069502), 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-1H-tetrazol-1-yl]methyl}-1H-pyrazole-5-carboxamide (known from WO2010/069502), N-[2-(tert-butylcarbamoyl)-4-cyano-6-methylphenyl]-1-(3-chloropyridin-2-yl)-3-{[5-(trifluoromethyl)-2H-tetrazol-2-yl]methyl}-1H-pyrazole-5-carboxamide (known from WO2010/069502), (1E)-N-[(6-chloropyridin-3-yl)methyl]-N'-cyano-N-(2,2-difluoroethyl)ethanimidamide (known from WO2008/009360), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), and methyl 2-[3,5-dibromo-2-({[3-bromo-1-(3-chloropyridin-2-yl)-1H-pyrazol-5-yl]carbonyl}amino)benzoyl]-2-ethyl-1-methylhydrazinecarboxylate (known from WO2011/049233).

A mixture with other known active compounds such as herbicides, or with fertilizers and growth regulators, safeners or semiochemicals is also possible.

In addition, the compounds of the formula (I) according to the invention also have very good antimycotic activity. They have a very broad antimycotic spectrum of action, in particular against dermatophytes and budding fungi, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The enumeration of these fungi is no restriction whatsoever of the mycotic spectrum which can be controlled and is provided by illustration only.

The compounds of formula (I) and the fungicide composition according to the invention can be used to curatively or preventively control the phytopathogenic fungi of plants or crops.

Thus, according to a further aspect of the invention, there is provided a method for curatively or preventively controlling the phytopathogenic fungi of plants or crops characterised in that a compound of formula (I) or a fungicide composition according to the invention is applied to the seed, the plant or to the fruit of the plant or to the soil wherein the plant is growing or wherein it is desired to grow.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the overground parts of the plant such as trunks, stems or stalks, leaves, flowers and fruit of the concerned plant.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts. Among the plants that can be protected by the method according to the invention, mention may be made of major field crops like corn, soybean, cotton, *Brassica* oilseeds such as *Brassica napus* (e.g. canola), *Brassica rapa, B. juncea* (e.g. mustard) and *Brassica carinata*, rice, wheat, sugarbeet, sugarcane, oats, rye, barley, millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans beans—such as climbing beans and broad beans), *Chenopodiaceae* sp. (for instance mangold, spinach beet, spinach, beetroots), *Malvaceae* (for instance okra), *Aspar-*

*agaceae* (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 or 12/497,221.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Examples of plants with the above-mentioned traits are non-exhaustively listed in Table A.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an Eleusine EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024,782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943,801 or 12/362,774. Plants comprising other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665. Further herbicide-tolerant plants are also plants that are made tolerant to the herbicides inhibiting the enzyme hydroxphenylpyruvatedioxygenase (HPPD). Hydroxphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 2009/144079, WO 2002/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate deshydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024,782 and U.S. Patent Application No. 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002,433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, and 6,013,861, WO 94/04693, WO 94/09144, WO 94/11520, WO 95/35026, WO 97/20936

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. Nos. 6,284,479, and 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:
a) Plants, such as cotton plants, containing an altered form of cellulose synthase genes as described in WO 98/00549
b) Plants, such as cotton plants, containing an altered form of rsw2 or rsw3 homologous nucleic acids as described in WO 2004/053219
c) Plants, such as cotton plants, with increased expression of sucrose phosphate synthase as described in WO 01/17333
d) Plants, such as cotton plants, with increased expression of sucrose synthase as described in WO 02/45485
e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938 f) Plants, such as cotton plants, having fibers with altered reactivity, e.g. through the expression of N-acetylglucosaminetransferase gene including nodC and chitin synthase genes as described in WO 2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants contain a mutation imparting such altered oil profile characteristics and include:
a) Plants, such as oilseed rape plants, producing oil having a high oleic acid content as described e.g. in U.S. Pat. Nos. 5,969,169, 5,840,946 or 6,323,392 or 6,063,947
b) Plants such as oilseed rape plants, producing oil having a low linolenic acid content as described in U.S. Pat. Nos. 6,270,828, 6,169,190, or 5,965,755
c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Appl. No. 61/135,230 WO09/068,313 and WO10/006,732. Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.ag-bios.com/dbase.php).

Further particularly transgenic plants include plants containing a transgene in an agronomically neutral or beneficial position as described in any of the patent publications listed in Table C.

TABLE A

| Trait | Reference | |
|---|---|---|
| Water use efficiency | WO 2000/073475 | |
| Nitrogen use efficiency | WO 1995/009911 | WO 2007/076115 |
| | WO 1997/030163 | WO 2005/103270 |
| | WO 2007/092704 | WO 2002/002776 |
| Improved photosynthesis | WO 2008/056915 | WO 2004/101751 |
| Nematode resistance | WO 1995/020669 | WO 2003/033651 |
| | WO 2001/051627 | WO 1999/060141 |
| | WO 2008/139334 | WO 1998/012335 |
| | WO 2008/095972 | WO 1996/030517 |
| | WO 2006/085966 | WO 1993/018170 |

TABLE A-continued

| Trait | Reference | |
|---|---|---|
| Reduced pod dehiscence | WO 2006/009649 | WO 1997/013865 |
| | WO 2004/113542 | WO 1996/030529 |
| | WO 1999/015680 | WO 1994/023043 |
| | WO 1999/000502 | |
| Aphid resistance | WO 2006/125065 | WO 2008/067043 |
| | WO 1997/046080 | WO 2004/072109 |
| Sclerotinia resistance | WO 2006/135717 | WO 2005/000007 |
| | WO 2006/055851 | WO 2002/099385 |
| | WO 2005/090578 | WO 2002/061043 |
| Botrytis resistance | WO 2006/046861 | WO 2002/085105 |
| Bremia resistance | US 20070022496 | WO 2004/049786 |
| | WO 2000/063432 | |
| Erwinia resistance | WO 2004/049786 | |
| Closterovirus resistance | WO 2007/073167 | WO 2002/022836 |
| | WO 2007/053015 | |
| Stress tolerance (including drought tolerance) | WO 2010/019838 | WO2008/002480 |
| | WO 2009/049110 | WO2005/033318 |
| Tobamovirus resistance | WO 2006/038794 | |

TABLE B

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| Petitions for Nonregulated Status Pending | | | | | |
| 10-070-01p | | Virginia Tech | Peanut | Sclerotinia blight resistant | N70, P39, and W171 |
| 09-349-01p | | Dow AgroSciences | Soybean | Herbicide Tolerant | DAS-68416-4 |
| 09-328-01p | | Bayer Crop Science | Soybean | Herbicide Tolerant | FG72 |
| 09-233-01p | | Dow | Corn | Herbicide Tolerant | DAS-40278-9 |
| 09-201-01p | | Monsanto | Soybean | | MON-877Ø5-6 |
| 09-183-01p | | Monsanto | Soybean | | MON-87769 |
| 09-082-01p | | Monsanto | Soybean | Lepidopteran resistant | MON 87701 |
| 09-063-01p | | Stine Seed | Corn | Glyphosate tolerant | HCEM485 |
| 09-055-01p | | Monsanto | Corn | Drought Tolerant | MON 87460 |
| 09-015-01p | | BASF Plant Science, LLC | Soybean | Herbicide Tolerant | BPS-CV127-9 Soybean |
| 08-366-01p | | ArborGen | Eucalyptus | Freeze Tolerant, Fertility Altered | ARB-FTE1-08 |
| 08-340-01p | | Bayer | Cotton | Glufosinate Tolerant, Insect Resistant | T304-40XGHB119 |
| 08-338-01p | | Pioneer | Corn | Male Sterile, Fertility Restored, Visual Marker | DP-32138-1 |
| 08-315-01p | | Florigene | Rose | Altered Flower Color | IFD-524Ø1-4 and IFD-529Ø1-9 |
| 07-253-01p | | Syngenta | Corn | Lepidopteran resistant | MIR-162 Maize |
| 07-108-01p | | Syngenta | Cotton | Lepidopteran Resistant | COT67B |
| 06-354-01p | | Pioneer | Soybean | High Oleic Acid | DP-3Ø5423-1 |
| 05-280-01p | | Syngenta | Corn | Thermostable alpha-amylase | 3272 |
| 04-110-01p | | Monsanto & Forage Genetics | Alfalfa | Glyphosate Tolerant | J101, J163 |
| 03-104-01p | | Monsanto & Scotts | Creeping bentgrass | Glyphosate Tolerant | ASR368 |
| Petitions for Nonregulated Status Granted | | | | | |
| 07-152-01p | | Pioneer | Corn | glyphosate & Imidazolinone tolerant | DP-098140-6 |
| 04-337-01p | | University of Florida | Papaya | Papaya Ringspot Virus Resistant | X17-2 |
| 06-332-01p | | Bayer CropScience | Cotton | Glyphosate tolerant | GHB614 |
| 06-298-01p | | Monsanto | Corn | European Corn Borer resistant | MON 89034 |

TABLE B-continued

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| 06-271-01p | | Pioneer | Soybean | Glyphosate & acetolactate synthase tolerant | 356043 (DP-356Ø43-5) |
| 06-234-01p | 98-329-01p | Bayer CropScience | Rice | Phosphinothricin tolerant | LLRICE601 |
| 06-178-01p | | Monsanto | Soybean | Glyphosate tolerant | MON 89788 |
| 04-362-01p | | Syngenta | Corn | Corn Rootworm Protected | MIR604 |
| 04-264-01p | | ARS | Plum | Plum Pox Virus Resistant | C5 |
| 04-229-01p | | Monsanto | Corn | High Lysine | LY038 |
| 04-125-01p | | Monsanto | Corn | Corn Rootworm Resistant | 88017 |
| 04-086-01p | | Monsanto | Cotton | Glyphosate Tolerant | MON 88913 |
| 03-353-01p | | Dow | Corn | Corn Rootworm Resistant | 59122 |
| 03-323-01p | | Monsanto | Sugar Beet | Glyphosate Tolerant | H7-1 |
| 03-181-01p | 00-136-01p | Dow | Corn | Lepidopteran Resistant & Phosphinothricin tolerant | TC-6275 |
| 03-155-01p | | Syngenta | Cotton | Lepidopteran Resistant | COT 102 |
| 03-036-01p | | Mycogen/Dow | Cotton | Lepidopteran Resistant | 281-24-236 |
| 03-036-02p | | Mycogen/Dow | Cotton | Lepidopteran Resistant | 3006-210-23 |
| 02-042-01p | | Aventis | Cotton | Phosphinothericin tolerant | LLCotton25 |
| 01-324-01p | 98-216-01p | Monsanto | Rapeseed | Glyphosate tolerant | RT200 |
| 01-206-01p | 98-278-01p | Aventis | Rapeseed | Phosphinothricin tolerant & pollination control | MS1 & RF1/RF2 |
| 01-206-02p | 97-205-01p | Aventis | Rapeseed | Phosphinothricin tolerant | Topas 19/2 |
| 01-137-01p | | Monsanto | Corn | Corn Rootworm Resistant | MON 863 |
| 01-121-01p | | Vector | Tobacco | Reduced nicotine | Vector 21-41 |
| 00-342-01p | | Monsanto | Cotton | Lepidopteran resistant | Cotton Event 15985 |
| 00-136-01p | | Mycogen c/o Dow & Pioneer | Corn | Lepidopteran resistant phosphinothricin tolerant | Line 1507 |
| 00-011-01p | 97-099-01p | Monsanto | Corn | Glyphosate tolerant | NK603 |
| 99-173-01p | 97-204-01p | Monsanto | Potato | PLRV & CPB resistant | RBMT22-82 |
| 98-349-01p | 95-228-01p | AgrEvo | Corn | Phosphinothricin tolerant and Male sterile | MS6 |
| 98-335-01p | | U. of Saskatchewan | Flax | Tolerant to soil residues of sulfonyl urea herbicide | CDC Triffid |
| 98-329-01p | | AgrEvo | Rice | Phosphinothricin tolerant | LLRICE06, LLRICE62 |
| 98-278-01p | | AgrEvo | Rapeseed | Phosphinothricin tolerant & Pollination control | MS8 & RF3 |
| 98-238-01p | | AgrEvo | Soybean | Phosphinothricin tolerant | GU262 |
| 98-216-01p | | Monsanto | Rapeseed | Glyphosate tolerant | RT73 |
| 98-173-01p | | Novartis Seeds & Monsanto | Beet | Glyphosate tolerant | GTSB77 |
| 98-014-01p | 96-068-01p | AgrEvo | Soybean | Phosphinothricin tolerant | A5547-127 |
| 97-342-01p | | Pioneer | Corn | Male sterile & Phosphinothricin tolerant | 676, 678, 680 |
| 97-339-01p | | Monsanto | Potato | CPB & PVY resistant | RBMT15-101, SEMT15-02, SEMT15-15 |
| 97-336-01p | | AgrEvo | Beet | Phosphinothricin tolerant | T-120-7 |
| 97-287-01p | | Monsanto | Tomato | Lepidopteran resistant | 5345 |
| 97-265-01p | | AgrEvo | Corn | Phosphinothricin tolerant & Lep. resistant | CBH-351 |

TABLE B-continued

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| 97-205-01p | | AgrEvo | Rapeseed | Phosphinothricin tolerant | T45 |
| 97-204-01p | | Monsanto | Potato | CPB & PLRV resistant | RBMT21-129 & RBMT21-350 |
| 97-148-01p | | Bejo | *Cichorium intybus* | Male sterile | RM3-3, RM3-4, RM3-6 |
| 97-099-01p | | Monsanto | Corn | Glyphosate tolerant | GA21 |
| 97-013-01p | | Calgene | Cotton | Bromoxynil tolerant & Lepidopteran resistant | Events 31807 & 31808 |
| 97-008-01p | | Du Pont | Soybean | Oil profile altered | G94-1, G94-19, G-168 |
| 96-317-01p | | Monsanto | Corn | Glyphosate tolerant & ECB resistant | MON802 |
| 96-291-01p | | DeKalb | Corn | European Corn Borer resistant | DBT418 |
| 96-248-01p | 92-196-01p | Calgene | Tomato | Fruit ripening altered | 1 additional FLAVRSAVR line |
| 96-068-01p | | AgrEvo | Soybean | Phosphinothricin tolerant | W62, W98, A2704-12, A2704-21, A5547-35 |
| 96-051-01p | | Cornell U | Papaya | PRSV resistant | 55-1, 63-1 |
| 96-017-01p | 95-093-01p | Monsanto | Corn | European Corn Borer resistant | MON809 & MON810 |
| 95-352-01p | | Asgrow | Squash | CMV, ZYMV, WMV2 resistant | CZW-3 |
| 95-338-01p | | Monsanto | Potato | CPB resistant | SBT02-5 & -7, ATBT04-6 &-27, -30, -31, -36 |
| 95-324-01p | | Agritope | Tomato | Fruit ripening altered | 35 1 N |
| 95-256-01p | | Du Pont | Cotton | Sulfonylurea tolerant | 19-51a |
| 95-228-01p | | Plant Genetic Systems | Corn | Male sterile | MS3 |
| 95-195-01p | | Northrup King | Corn | European Corn Borer resistant | Bt11 |
| 95-179-01p | 92-196-01p | Calgene | Tomato | Fruit ripening altered | 2 additional FLAVRSAVR lines |
| 95-145-01p | | DeKalb | Corn | Phosphinothricin tolerant | B16 |
| 95-093-01p | | Monsanto | Corn | Lepidopteran resistant | MON 80100 |
| 95-053-01p | | Monsanto | Tomato | Fruit ripening altered | 8338 |
| 95-045-01p | | Monsanto | Cotton | Glyphosate tolerant | 1445, 1698 |
| 95-030-01p | 92-196-01p | Calgene | Tomato | Fruit ripening altered | 20 additional FLAVRSAVR lines |
| 94-357-01p | | AgrEvo | Corn | Phosphinothricin tolerant | T14, T25 |
| 94-319-01p | | Ciba Seeds | Corn | Lepidopteran resistant | Event 176 |
| 94-308-01p | | Monsanto | Cotton | Lepidopteran resistant | 531, 757, 1076 |
| 94-290-01p | | Zeneca & Petoseed | Tomato | Fruit polygalacturonase level decreased | B, Da, F |
| 94-257-01p | | Monsanto | Potato | Coleopteran resistant | BT6, BT10, BT12, BT16, BT17, BT18, BT23 |
| 94-230-01p | 92-196-01p | Calgene | Tomato | Fruit ripening altered | 9 additional FLAVRSAVR lines |
| 94-228-01p | | DNA Plant Tech | Tomato | Fruit ripening altered | 1345-4 |
| 94-227-01p | 92-196-01p | Calgene | Tomato | Fruit ripening altered | Line N73 1436-111 |
| 94-090-01p | | Calgene | Rapeseed | Oil profile altered | pCGN3828-212/86- 18 & 23 |

TABLE B-continued

Petitions of Nonregulated Status Granted or Pending by APHIS as of Mar. 31, 2010

Applicant Documents

| Petition | Extension of Petition Number *** | Institution | Regulated Article | Transgenic Phenotype | Transformation Event or Line |
|---|---|---|---|---|---|
| 93-258-01p | | Monsanto | Soybean | Glyphosate tolerant | 40-3-2 |
| 93-196-01p | | Calgene | Cotton | Bromoxynil tolerant | BXN |
| 92-204-01p | | Upjohn | Squash | WMV2 & ZYMV resistant | ZW-20 |
| 92-196-01p | | Calgene | Tomato | Fruit ripening altered | FLAVR SAVR |

NOTE:
To obtain the most up-to-date list of Crops No Longer Regulated, please look at the Current Status of Petitions. This list is automatically updated and reflects all petitions received to date by APHIS, including petitions pending, withdrawn, or approved.
Abbreviations:
CMV—cucumber mosaic virus; CPB—colorado potato beetle; PLRV—potato leafroll virus; PRSV—papaya ringspot virus; PVY—potato virus Y; WMV2—watermelon mosaic virus 2 ZYMV—zucchini yellow mosaic virus
*** Extension of Petition Number: Under 7CFR 340.6(e) a person may request that APHIS extend a determination of non-regulated status to other organisms based on their similarity of the previously deregulated article. This column lists the previously granted petition of that degregulated article.
**** Preliminary EA: The Environmental Assessment initially available for Public comment prior to finalization.

TABLE C

| Plant species | Event | Trait | Patent reference |
|---|---|---|---|
| Corn | PV-ZMGT32 (NK603) | Glyphosate tolerance | US 2007-056056 |
| Corn | MIR604 | Insect resistance (Cry3a055) | EP 1 737 290 |
| Corn | LY038 | High lysine content | U.S. Pat. No. 7,157,281 |
| Corn | 3272 | Self processing corn (alpha-amylase) | US 2006-230473 |
| Corn | PV-ZMIR13 (MON863) | Insect resistance (Cry3Bb) | US 2006-095986 |
| Corn | DAS-59122-7 | Insect resistance (Cry34Ab1/Cry35Ab1) | US 2006-070139 |
| Corn | TC1507 | Insect resistance (Cry1F) | U.S. Pat. No. 7,435,807 |
| Corn | MON810 | Insect resistance (Cry1Ab) | US 2004-180373 |
| Corn | VIP1034 | Insect resistance | WO 03/052073 |
| Corn | B16 | Glufosinate resistance | US 2003-126634 |
| Corn | GA21 | Glyphosate resistance | U.S. Pat. No. 6,040,497 |
| Corn | GG25 | Glyphosate resistance | U.S. Pat. No. 6,040,497 |
| Corn | GJ11 | Glyphosate resistance | U.S. Pat. No. 6,040,497 |
| Corn | FI117 | Glyphosate resistance | U.S. Pat. No. 6,040,497 |
| Corn | GAT-ZM1 | Glufosinate tolerance | WO 01/51654 |
| Corn | MON87460 | Drought tolerance | WO 2009/111263 |
| Corn | DP-098140-6 | Glyphosate tolerance/ALS inhibitor tolerance | WO 2008/112019 |
| Wheat | Event 1 | Fusarium resistance (trichothecene 3-O-acetyltransferase) | CA 2561992 |
| Sugar beet | T227-1 | Glyphosate tolerance | US 2004-117870 |
| Sugar beet | H7-1 | Glyphosate tolerance | WO 2004-074492 |
| Soybean | MON89788 | Glyphosate tolerance | US 2006-282915 |
| Soybean | A2704-12 | Glufosinate tolerance | WO 2006/108674 |
| Soybean | A5547-35 | Glufosinate tolerance | WO 2006/108675 |
| Soybean | DP-305423-1 | High oleic acid/ALS inhibitor tolerance | WO 2008/054747 |
| Rice | GAT-OS2 | Glufosinate tolerance | WO 01/83818 |
| Rice | GAT-OS3 | Glufosinate tolerance | US 2008-289060 |
| Rice | PE-7 | Insect resistance (Cry1Ac) | WO 2008/114282 |
| Oilseed rape | MS-B2 | Male sterility | WO 01/31042 |
| Oilseed rape | MS-BN1/RF-BN1 | Male sterility/restoration | WO 01/41558 |
| Oilseed rape | RT73 | Glyphosate resistance | WO 02/36831 |
| Cotton | CE43-67B | Insect resistance (Cry1Ab) | WO 2006/128573 |
| Cotton | CE46-02A | Insect resistance (Cry1Ab) | WO 2006/128572 |
| Cotton | CE44-69D | Insect resistance (Cry1Ab) | WO 2006/128571 |
| Cotton | 1143-14A | Insect resistance (Cry1Ab) | WO 2006/128569 |
| Cotton | 1143-51B | Insect resistance (Cry1Ab) | WO 2006/128570 |
| Cotton | T342-142 | Insect resistance (Cry1Ab) | WO 2006/128568 |
| Cotton | event3006-210-23 | Insect resistance (Cry1Ac) | WO 2005/103266 |
| Cotton | PV-GHGT07 (1445) | Glyphosate tolerance | US 2004-148666 |
| Cotton | MON88913 | Glyphosate tolerance | WO 2004/072235 |
| Cotton | EE-GH3 | Glyphosate tolerance | WO 2007/017186 |
| Cotton | T304-40 | Insect-resistance (Cry1Ab) | WO2008/122406 |
| Cotton | Cot202 | Insect resistance (VIP3) | US 2007-067868 |
| Cotton | LLcotton25 | Glufosinate resistance | WO 2007/017186 |

TABLE C-continued

| Plant species | Event | Trait | Patent reference |
|---|---|---|---|
| Cotton | EE-GH5 | Insect resistance (Cry1Ab) | WO 2008/122406 |
| Cotton | event 281-24-236 | Insect resistance (Cry1F) | WO 2005/103266 |
| Cotton | Cot102 | Insect resistance (Vip3A) | US 2006-130175 |
| Cotton | MON 15985 | Insect resistance (Cry1A/Cry2Ab) | US 2004-250317 |
| Bent Grass | Asr-368 | Glyphosate tolerance | US 2006-162007 |
| Brinjal | EE-1 | Insect resistance (Cry1Ac) | WO 2007/091277 |

Among the diseases of plants or crops that can be controlled by the method according to the invention, mention can be made of:

Powdery mildew diseases such as:
  *Blumeria* diseases, caused for example by *Blumeria graminis*;
  *Podosphaera* diseases, caused for example by *Podosphaera leucotricha*;
  *Sphaerotheca* diseases, caused for example by *Sphaerotheca fuliginea*;
  *Uncinula* diseases, caused for example by *Uncinula necator*;

Rust diseases such as:
  *Gymnosporangium* diseases, caused for example by *Gymnosporangium sabinae*;
  *Hemileia* diseases, caused for example by *Hemileia vastatrix*;
  *Phakopsora* diseases, caused for example by *Phakopsora pachyrhizi* or *Phakopsora meibomiae*;
  *Puccinia* diseases, caused for example by *Puccinia recondite*, *Puccinia graminis* or *Puccinia striiformis*;
  *Uromyces* diseases, caused for example by *Uromyces appendiculatus*;

Oomycete diseases such as:
  *Albugo* diseases caused for example by *Albugo candida*;
  *Bremia* diseases, caused for example by *Bremia lactucae*;
  *Peronospora* diseases, caused for example by *Peronospora pisi* or *P. brassicae*;
  *Phytophthora* diseases, caused for example by *Phytophthora infestans*;
  *Plasmopara* diseases, caused for example by *Plasmopara viticola*;
  *Pseudoperonospora* diseases, caused for example by *Pseudoperonospora humuli* or *Pseudoperonospora cubensis*;
  *Pythium* diseases, caused for example by *Pythium ultimum*;

Leafspot, leaf blotch and leaf blight diseases such as:
  *Alternaria* diseases, caused for example by *Alternaria solani*;
  *Cercospora* diseases, caused for example by *Cercospora beticola*;
  *Cladiosporum* diseases, caused for example by *Cladiosporium cucumerinum*;
  *Cochliobolus* diseases, caused for example by *Cochliobolus sativus* (Conidiaform: *Drechslera*, Syn: *Helminthosporium*) or *Cochliobolus miyabeanus*;
  *Colletotrichum* diseases, caused for example by *Colletotrichum lindemuthanium*;
  *Cycloconium* diseases, caused for example by *Cycloconium oleaginum*;
  *Diaporthe* diseases, caused for example by *Diaporthe citri*;
  *Elsinoe* diseases, caused for example by *Elsinoe fawcettii*;
  *Gloeosporium* diseases, caused for example by *Gloeosporium laeticolor*;
  *Glomerella* diseases, caused for example by *Glomerella cingulata*;
  *Guignardia* diseases, caused for example by *Guignardia bidwelli*;
  *Leptosphaeria* diseases, caused for example by *Leptosphaeria maculans*; *Leptosphaeria nodorum*;
  *Magnaporthe* diseases, caused for example by *Magnaporthe grisea*;
  *Mycosphaerella* diseases, caused for example by *Mycosphaerella graminicola*; *Mycosphaerella arachidicola*; *Mycosphaerella fijiensis*;
  *Phaeosphaeria* diseases, caused for example by *Phaeosphaeria nodorum*;
  *Pyrenophora* diseases, caused for example by *Pyrenophora teres*, or *Pyrenophora tritici repentis*;
  *Ramularia* diseases, caused for example by *Ramularia collo-cygni*, or *Ramularia areola*;
  *Rhynchosporium* diseases, caused for example by *Rhynchosporium secalis*;
  *Septoria* diseases, caused for example by *Septoria apii* or *Septoria lycopercisi*;
  *Typhula* diseases, caused for example by *Typhula incamata*;
  *Venturia* diseases, caused for example by *Venturia inaequalis*;

Root, Sheath and stem diseases such as:
  *Corticium* diseases, caused for example by *Corticium graminearum*;
  *Fusarium* diseases, caused for example by *Fusarium oxysporum*;
  *Gaeumannomyces* diseases, caused for example by *Gaeumannomyces graminis*;
  *Rhizoctonia* diseases, caused for example by *Rhizoctonia solani*;
  *Sarocladium* diseases caused for example by *Sarocladium oryzae*;
  *Sclerotium* diseases caused for example by *Sclerotium oryzae*;
  *Tapesia* diseases, caused for example by *Tapesia acuformis*;
  *Thielaviopsis* diseases, caused for example by *Thielaviopsis basicola*;

Ear and panicle diseases such as:
  *Alternaria* diseases, caused for example by *Alternaria* spp.;
  *Aspergillus* diseases, caused for example by *Aspergillus flavus*;
  *Cladosporium* diseases, caused for example by *Cladosporium* spp.;
  *Claviceps* diseases, caused for example by *Claviceps purpurea*;
  *Fusarium* diseases, caused for example by *Fusarium culmorum*;

*Gibberella* diseases, caused for example by *Gibberella zeae*;
*Monographella* diseases, caused for example by *Monographella nivalis*;

Smut and bunt diseases such as:
  *Sphacelotheca* diseases, caused for example by *Sphacelotheca reiliana*;
  *Tilletia* diseases, caused for example by *Tilletia caries*;
  *Urocystis* diseases, caused for example by *Urocystis occulta*;
  *Ustilago* diseases, caused for example by *Ustilago nuda*;

Fruit rot and mould diseases such as:
  *Aspergillus* diseases, caused for example by *Aspergillus flavus*;
  *Botrytis* diseases, caused for example by *Botrytis cinerea*;
  *Penicillium* diseases, caused for example by *Penicillium expansum*;
  *Rhizopus* diseases caused by example by *Rhizopus stolonifer*
  *Sclerotinia* diseases, caused for example by *Sclerotinia sclerotiorum*;
  *Verticilium* diseases, caused for example by *Verticilium alboatrum*;

Seed and soilborne decay, mould, wilt, rot and damping-off diseases:
  *Alternaria* diseases, caused for example by *Alternaria brassicicola*
  *Aphanomyces* diseases, caused for example by *Aphanomyces euteiches*
  *Ascochyta* diseases, caused for example by *Ascochyta lentis*
  *Aspergillus* diseases, caused for example by *Aspergillus flavus*
  *Cladosporium* diseases, caused for example by *Cladosporium herbarum*
  *Cochliobolus* diseases, caused for example by *Cochliobolus sativus*
  (Conidiaform: *Drechslera, Bipolaris* Syn: *Helminthosporium*);
  *Colletotrichum* diseases, caused for example by *Colletotrichum coccodes*;
  *Fusarium* diseases, caused for example by *Fusarium culmorum*;
  *Gibberella* diseases, caused for example by *Gibberella zeae*;
  *Macrophomina* diseases, caused for example by *Macrophomina phaseolina*
  *Monographella* diseases, caused for example by *Monographella nivalis*;
  *Penicillium* diseases, caused for example by *Penicillium expansum*
  *Phoma* diseases, caused for example by *Phoma lingam*
  *Phomopsis* diseases, caused for example by *Phomopsis sojae*;
  *Phytophthora* diseases, caused for example by *Phytophthora cactorum*;
  *Pyrenophora* diseases, caused for example by *Pyrenophora graminea*
  *Pyricularia* diseases, caused for example by *Pyricularia oryzae*;
  *Pythium* diseases, caused for example by *Pythium ultimum*;
  *Rhizoctonia* diseases, caused for example by *Rhizoctonia solani*;
  *Rhizopus* diseases, caused for example by *Rhizopus oryzae*
  *Sclerotium* diseases, caused for example by *Sclerotium rolfsii*;
  *Septoria* diseases, caused for example by *Septoria nodorum*;
  *Typhula* diseases, caused for example by *Typhula incarnata*;
  *Verticillium* diseases, caused for example by *Verticillium dahliae*;

Canker, broom and dieback diseases such as:
  *Nectria* diseases, caused for example by *Nectria galligena*;

Blight diseases such as:
  *Monilinia* diseases, caused for example by *Monilinia laxa*;

Leaf blister or leaf curl diseases such as:
  *Exobasidium* diseases caused for example by *Exobasidium vexans*
  *Taphrina* diseases, caused for example by *Taphrina deformans*;

Decline diseases of wooden plants such as:
  *Esca* diseases, caused for example by *Phaemoniella clamydospora*;
  *Eutypa* dyeback, caused for example by *Eutypa lata*;
  *Ganoderma* diseases caused for example by *Ganoderma boninense*;
  *Rigidoporus* diseases caused for example by *Rigidoporus lignosus*

Diseases of Flowers and Seeds such as
  *Botrytis* diseases caused for example by *Botrytis cinerea*;

Diseases of Tubers such as
  *Rhizoctonia* diseases caused for example by *Rhizoctonia solani*;
  *Helminthosporium* diseases caused for example by *Helminthosporium solani*;

Club root diseases such as
  *Plasmodiophora* diseases, cause for example by *Plamodiophora brassicae*.

Diseases caused by Bacterial Organisms such as
  *Xanthomonas* species for example *Xanthomonas campestris* pv. *oryzae*;
  *Pseudomonas* species for example *Pseudomonas syringae* pv. *lachrymans*;
  *Erwinia* species for example *Erwinia amylovora*.

The composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention or a composition according to the invention; this includes for example direct application, spraying, dipping, injection or any other suitable means.

The dose of active compound usually applied in the method of treatment according to the invention is generally and advantageously from 10 to 800 g/ha, preferably from 50 to 300 g/ha for applications in foliar treatment. The dose of active substance applied is generally and advantageously from 2 to 200 g per 100 kg of seed, preferably from 3 to 150 g per 100 kg of seed in the case of seed treatment.

It is clearly understood that the doses indicated herein are given as illustrative examples of the method according to the invention. A person skilled in the art will know how to adapt the application doses, notably according to the nature of the plant or crop to be treated.

The compounds or mixtures according to the invention can also be used for the preparation of composition useful to curatively or preventively treat human or animal fungal diseases such as, for example, mycoses, dermatoses, trichophyton diseases and candidiases or diseases caused by *Aspergillus* spp., for example *Aspergillus fumigatus*.

The various aspects of the invention will now be illustrated with reference to the following table of compound examples and the following preparation or efficacy examples.

Table 1 illustrates in a non-limiting manner examples of compounds of formula (I) according to the invention.

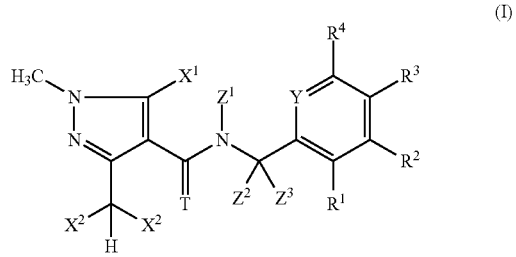

(I)

In table 1, M+H (Apcl+) means the molecular ion peak plus 1 a.m.u. (atomic mass unit) as observed in mass spectroscopy via positive atmospheric pressure chemical ionisation.

In table 1, the log P values were determined in accordance with EEC Directive 79/831 Annex V.A8 by HPLC (High Performance Liquid Chromatography) on a reversed-phase column (C 18), using the method described below:

Temperature: 40° C.; Mobile phases: 0.1% aqueous formic acid and acetonitrile; linear gradient from 10% acetonitrile to 90% acetonitrile.

Calibration was carried out using unbranched alkan-2-ones (comprising 3 to 16 carbon atoms) with known log P values (determination of the log P values by the retention times using linear interpolation between two successive alkanones). lambda-max-values were determined using UV-spectra from 200 nm to 400 nm and the peak values of the chromatographic signals.

TABLE 1

| Compound | $X^1$ | $X^2$ | T | $Z^1$ | $Z^2$ | $Z^3$ | $R^1$ | $R^2$ | $R^3$ | $R^4$ | Y | $R^5$ | logP | Mass M + H |
|---|---|---|---|---|---|---|---|---|---|---|---|---|---|---|
| 1 | Cl | F | O | H | Me | H | H | H | H | H | $CR^5$ | H | 2.49 | 314 |
| 2 | F | F | O | H | Me | H | H | H | H | H | $CR^5$ | H | 2.33 | 298 |
| 3 | F | F | O | H | CN | H | H | H | H | H | $CR^5$ | H | 2.07 | |
| 4 | Cl | F | O | H | CN | H | H | H | H | H | $CR^5$ | H | 2.20 | |
| 5 | Cl | F | O | Me | H | H | Me | H | H | H | $CR^5$ | Me | 3.02 | 342 |
| 6 | F | F | O | Me | H | H | Me | H | H | H | $CR^5$ | Me | 2.84 | 326 |
| 7 | Cl | F | O | H | CN | H | F | H | H | F | $CR^5$ | H | 2.31 | |
| 8 | F | F | O | H | CN | H | F | H | H | F | $CR^5$ | H | 2.01 | |
| 9 | F | F | O | H | Me | Me | F | H | H | H | $CR^5$ | F | 4.19 | 348 |
| 10 | Cl | F | O | H | Me | Me | F | H | H | H | $CR^5$ | F | 3.89 | 364 |
| 11 | F | F | O | cyanomethyl | H | H | Et | H | H | H | $CR^5$ | H | 2.68 | 351 |
| 12 | F | F | O | cyclobutyl | H | H | Et | H | H | H | $CR^5$ | H | 3.63 | 366 |
| 13 | F | F | O | Et | H | H | Et | H | H | H | $CR^5$ | H | 3.13 | 340 |
| 14 | F | F | O | i-Pr [(1)] | H | H | Et | H | H | H | $CR^5$ | H | 3.39 | 354 |
| 15 | F | F | O | Me | H | H | Et | H | H | H | $CR^5$ | H | 2.81 | 326 |
| 16 | F | F | O | allyl | H | H | Et | H | H | H | $CR^5$ | H | 3.36 | 352 |
| 17 | F | F | O | propargyl | H | H | Et | H | H | H | $CR^5$ | H | 3.10 | 350 |
| 18 | F | F | S | Me | Me | H | Cl | H | H | H | $CR^5$ | H | 3.44 | 362 |
| 19 | Cl | F | O | H | $CF_3$ | H | Cl | H | H | H | $CR^5$ | H | 3.33 | 402 |
| 20 | Cl | F | O | H | Me | H | Cl | H | H | H | $CR^5$ | H | 2.92 | 348 |
| 21 | Cl | F | O | H | H | H | Cl | H | H | H | $CR^5$ | H | 2.69 | 334 |
| 22 | Cl | F | O | H | Me | Me | Cl | H | H | H | $CR^5$ | H | 3.15 | 362 |
| 23 | F | F | O | H | $CF_3$ | H | Cl | H | H | H | $CR^5$ | H | 3.21 | 386 |
| 24 | F | F | O | H | Me | H | Cl | H | H | H | $CR^5$ | H | 2.75 | 332 |
| 25 | F | F | O | H | H | H | Cl | H | H | H | $CR^5$ | H | 2.50 | 318 |
| 26 | F | F | O | H | Me | Me | Cl | H | H | H | $CR^5$ | H | 2.92 | 346 |
| 27 | Cl | F | O | Me | Me | H | Cl | H | H | H | $CR^5$ | H | 2.84 | 362 |
| 28 | F | F | O | Me | Me | H | Cl | H | H | H | $CR^5$ | H | 2.68 | 346 |
| 29 | F | F | O | H | Me | H | Cl | Cl | H | H | $CR^5$ | H | 3.13 | 366 |
| 30 | Cl | F | O | cyclobutyl | H | H | Cl | H | Cl | H | $CR^5$ | H | 4.39 | 422 |
| 31 | F | F | O | cyclobutyl | H | H | Cl | H | Cl | H | $CR^5$ | H | 4.19 | 406 |
| 32 | Cl | F | O | H | $CF_3$ | H | Cl | H | Cl | H | $CR^5$ | H | 3.89 | 436 |
| 33 | Cl | F | O | H | Me | H | Cl | H | Cl | H | $CR^5$ | H | 4.39 | 382 |
| 34 | Cl | F | O | H | H | H | Cl | H | Cl | H | $CR^5$ | H | 4.19 | 368 |
| 35 | Cl | F | O | H | Me | Me | Cl | H | Cl | H | $CR^5$ | H | 3.89 | 396 |
| 36 | F | F | O | H | Me | H | Cl | H | Cl | H | $CR^5$ | H | 4.39 | 366 |
| 37 | F | F | O | H | H | H | Cl | H | Cl | H | $CR^5$ | H | 4.19 | 352 |
| 38 | F | F | O | H | —$CH_2CH_2$— | | Cl | H | Cl | H | $CR^5$ | H | 3.89 | 378 |
| 39 | F | F | O | H | Me | Me | Cl | H | Cl | H | $CR^5$ | H | 4.39 | 380 |
| 40 | F | F | O | H | $CF_3$ | H | Cl | H | Cl | H | $CR^5$ | H | 4.19 | 420 |
| 41 | Cl | F | O | H | —$CH_2CH_2$— | | Cl | H | Cl | H | $CR^5$ | H | 3.89 | 394 |
| 42 | Cl | F | O | Me | H | H | Cl | H | Cl | H | $CR^5$ | H | 3.37 | 382 |
| 43 | F | F | O | Me | H | H | Cl | H | Cl | H | $CR^5$ | H | 3.19 | 366 |
| 44 | Cl | F | S | H | Me | H | Cl | H | Cl | H | $CR^5$ | H | 3.99 | 398 |
| 45 | F | F | O | OMe | Me | H | Cl | H | Cl | H | $CR^5$ | H | 3.65 | 396 |
| 46 | Cl | F | O | OMe | Me | H | Cl | H | Cl | H | $CR^5$ | H | 3.81 | 412 |
| 47 | Cl | F | O | H | H | H | Cl | H | H | Cl | $CR^5$ | H | 4.39 | 368 |
| 48 | Cl | F | O | H | —$CH_2CH_2$— | | Cl | H | H | Cl | $CR^5$ | H | 4.19 | 394 |
| 49 | Cl | F | O | H | Me | Me | Cl | H | H | Cl | $CR^5$ | H | 3.89 | 396 |
| 50 | Cl | F | O | H | Me | H | Cl | H | H | Cl | $CR^5$ | H | 4.39 | 382 |
| 51 | F | F | O | H | —$CH_2CH_2$— | | Cl | H | H | Cl | $CR^5$ | H | 4.19 | 378 |
| 52 | F | F | O | H | Me | Me | Cl | H | H | Cl | $CR^5$ | H | 3.89 | 380 |
| 53 | F | F | O | H | Me | H | Cl | H | H | Cl | $CR^5$ | H | 4.39 | 366 |
| 54 | F | F | O | H | H | H | Cl | H | H | Cl | $CR^5$ | H | 4.19 | 352 |

TABLE 1-continued

| Compound | $X^1$ | $X^2$ | T | $Z^1$ | $Z^2$ | $Z^3$ | $R^1$ | $R^2$ | $R^3$ | $R^4$ | Y | $R^5$ | logP | Mass M + H |
|---|---|---|---|---|---|---|---|---|---|---|---|---|---|---|
| 55 | Cl | F | O | Me | Me | H | Cl | H | H | Cl | $CR^5$ | H | 3.33 | 396 |
| 56 | F | F | O | Me | Me | H | Cl | H | H | Cl | $CR^5$ | H | 3.15 | 380 |
| 57 | Cl | F | O | Me | H | H | Cl | H | H | Cl | $CR^5$ | H | 3.23 | 382 |
| 58 | F | F | O | Me | H | H | Cl | H | H | Cl | $CR^5$ | H | 3.02 | 366 |
| 59 | Cl | F | O | H | H | H | Cl | H | H | H | $CR^5$ | Cl | 3.89 | 368 |
| 60 | F | F | O | H | H | H | Cl | H | H | H | $CR^5$ | Cl | 4.39 | 352 |
| 61 | Cl | F | O | Me | H | H | Cl | H | H | H | $CR^5$ | Cl | 3.02 | 382 |
| 62 | F | F | O | Me | H | H | Cl | H | H | H | $CR^5$ | Cl | 2.82 | 366 |
| 63 | Cl | F | O | Me | Me | H | Cl | H | H | H | $CR^5$ | Cl | 3.25 | 396 |
| 64 | F | F | O | Me | Me | H | Cl | H | H | H | $CR^5$ | Cl | 3.13 | 380 |
| 65 | F | F | O | H | H | H | c-Pr [(1)] | H | H | H | $CR^5$ | H | 2.78 | 324 |
| 66 | Cl | F | O | H | H | H | c-Pr | H | H | H | $CR^5$ | H | 2.98 | 340 |
| 67 | F | F | O | cyanomethyl | H | H | i-Pr | H | H | H | $CR^5$ | H | 2.94 | 365 |
| 68 | F | F | O | Et | H | H | i-Pr | H | H | H | $CR^5$ | H | 3.42 | 354 |
| 69 | F | F | O | i-Pr | H | H | i-Pr | H | H | H | $CR^5$ | H | 3.70 | 368 |
| 70 | F | F | O | cyclobutyl | H | H | i-Pr | H | H | H | $CR^5$ | H | 3.90 | 380 |
| 71 | F | F | O | allyl | H | H | i-Pr | H | H | H | $CR^5$ | H | 3.66 | 366 |
| 72 | F | F | O | Me | H | H | i-Pr | H | H | H | $CR^5$ | H | 3.11 | 340 |
| 73 | F | F | O | propargyl | H | H | i-Pr | H | H | H | $CR^5$ | H | 3.37 | 364 |
| 74 | F | F | O | H | H | H | i-Pr | H | H | H | $CR^5$ | H | 3.02 | 326 |
| 75 | F | F | S | cyclobutyl | H | H | i-Pr | H | H | H | $CR^5$ | H | 4.63 | 396 |
| 76 | F | F | O | OMe | H | H | i-Pr | H | H | H | $CR^5$ | H | 3.37 | 356 |
| 77 | Cl | F | O | OMe | H | H | i-Pr | H | H | H | $CR^5$ | H | 3.51 | 372 |
| 78 | F | F | O | 2,2-difluoroethyl | H | H | i-Pr | H | H | H | $CR^5$ | H | 3.49 | |
| 79 | Cl | F | O | H | H | H | i-Pr | H | H | H | $CR^5$ | H | 3.19 | 342 |
| 80 | F | F | O | 2,2-difluoroethyl | H | H | i-Pr | H | H | Cl | $CR^5$ | H | 3.81 | |
| 81 | F | F | O | H | H | H | $CF_3$ | H | H | H | $CR^5$ | H | 2.76 | 352 |
| 82 | Cl | F | O | H | Me | H | $CF_3$ | H | H | H | $CR^5$ | H | 3.11 | 382 |
| 83 | Cl | F | O | H | H | H | $CF_3$ | H | H | H | $CR^5$ | H | 2.96 | 368 |
| 84 | F | F | O | H | Me | H | $CF_3$ | H | H | H | $CR^5$ | H | 2.96 | 366 |
| 85 | Cl | F | S | H | Me | H | $CF_3$ | H | H | H | $CR^5$ | H | 3.55 | 398 |
| 86 | Cl | F | O | 3-thietanyl | H | H | $CF_3$ | H | H | Cl | $CR^5$ | H | 4.08 | 474 |
| 87 | F | F | O | 3-thietanyl | H | H | $CF_3$ | H | H | Cl | $CR^5$ | H | 3.92 | 458 |
| 88 | F | F | O | cyanomethyl | H | H | $CF_3$ | H | H | H | $CR^5$ | Cl | 2.68 | 425 |
| 89 | F | F | O | Me | H | H | $CF_3$ | H | H | H | $CR^5$ | Cl | 2.93 | 400 |
| 90 | F | F | O | cyclobutyl | H | H | $CF_3$ | H | H | H | $CR^5$ | Cl | 3.81 | 440 |
| 91 | F | F | O | Et | H | H | $CF_3$ | H | H | H | $CR^5$ | Cl | 3.22 | 414 |
| 92 | F | F | O | i-Pr | H | H | $CF_3$ | H | H | H | $CR^5$ | Cl | 3.61 | 428 |
| 93 | F | F | O | propargyl | H | H | $CF_3$ | H | H | H | $CR^5$ | Cl | 3.05 | 424 |
| 94 | F | F | O | allyl | H | H | $CF_3$ | H | H | H | $CR^5$ | Cl | 3.37 | 426 |
| 95 | F | F | O | H | H | H | $CF_3$ | H | H | H | $CR^5$ | F | 2.69 | 370 |
| 96 | Cl | F | O | H | H | H | $CF_3$ | H | H | H | $CR^5$ | F | 2.86 | 386 |
| 97 | F | F | O | cyanomethyl | H | H | trimethyl-silyl | H | H | H | $CR^5$ | H | 3.52 | 395 |
| 98 | F | F | O | cyclobutyl | H | H | trimethyl-silyl | H | H | H | $CR^5$ | H | 4.61 | 410 |
| 99 | F | F | O | Et | H | H | trimethyl-silyl | H | H | H | $CR^5$ | H | 4.09 | 384 |
| 100 | F | F | O | allyl | H | H | trimethyl-silyl | H | H | H | $CR^5$ | H | 4.27 | 396 |
| 101 | F | F | O | propargyl | H | H | trimethyl-silyl | H | H | H | $CR^5$ | H | 3.93 | 394 |
| 102 | F | F | O | i-Pr | H | H | trimethyl-silyl | H | H | H | $CR^5$ | H | 4.37 | 398 |
| 103 | F | F | O | Me | H | H | trimethyl-silyl | H | H | H | $CR^5$ | H | 3.78 | 370 |
| 104 | Cl | F | O | Me | H | H | Br | H | H | H | $CR^5$ | H | 2.90 | 392 |
| 105 | F | F | O | Me | H | H | Br | H | H | H | $CR^5$ | H | 2.71 | 376 |
| 106 | Cl | F | O | H | H | H | $SCF_3$ | H | H | H | $CR^5$ | H | 3.29 | 400 |
| 107 | F | F | O | H | H | H | $SCF_3$ | H | H | H | $CR^5$ | H | 3.11 | 384 |
| 108 | F | F | O | H | —[CH$_2$]$_4$— | | H | $CF_3$ | H | H | $CR^5$ | H | 3.65 | 406 |
| 109 | Cl | F | O | H | —[CH$_2$]$_4$— | | H | $CF_3$ | H | H | $CR^5$ | H | 3.80 | 422 |
| 110 | F | F | O | H | H | H | H | —CH$_2$CH$_2$CH$_2$CH$_2$— | | H | $CR^5$ | H | 3.25 | 338 |
| 111 | Cl | F | O | H | H | H | H | —CH$_2$CH$_2$CH$_2$CH$_2$— | | H | $CR^5$ | H | 3.44 | 354 |
| 112 | Cl | F | O | H | Me | Me | H | Cl | H | Cl | $CR^5$ | H | 3.73 | 396 |
| 113 | Cl | F | O | H | H | H | H | Cl | H | Cl | $CR^5$ | H | 3.23 | 368 |
| 114 | F | F | O | H | Me | Me | H | Cl | H | Cl | $CR^5$ | H | 3.59 | 380 |
| 115 | F | F | O | H | H | H | H | Cl | H | Cl | $CR^5$ | H | 3.09 | 352 |
| 116 | Cl | F | O | Me | Me | H | H | Cl | H | Cl | $CR^5$ | H | 3.65 | 396 |
| 117 | F | F | O | Me | Me | H | H | Cl | H | Cl | $CR^5$ | H | 3.46 | 380 |
| 118 | F | F | S | Me | Me | H | H | Cl | H | Cl | $CR^5$ | H | 4.24 | 396 |
| 119 | F | F | O | H | H | H | H | OMe | OMe | H | $CR^5$ | H | 1.79 | 344 |
| 120 | Cl | F | O | H | H | H | H | OMe | OMe | H | $CR^5$ | H | 1.36 | 360 |
| 121 | F | F | O | H | —[CH$_2$]$_4$— | | H | H | $CF_3$ | H | $CR^5$ | H | 3.72 | 406 |
| 122 | Cl | F | O | H | —[CH$_2$]$_4$— | | H | H | $CF_3$ | H | $CR^5$ | H | 3.87 | 422 |
| 123 | F | F | O | H | H | H | H | H | $CF_3$ | H | $CR^5$ | H | 2.75 | 352 |

TABLE 1-continued

| Compound | $X^1$ | $X^2$ | T | $Z^1$ | $Z^2$ | $Z^3$ | $R^1$ | $R^2$ | $R^3$ | $R^4$ | Y | $R^5$ | logP | Mass M + H |
|---|---|---|---|---|---|---|---|---|---|---|---|---|---|---|
| 124 | Cl | F | O | H | H | H | H | H | $CF_3$ | H | $CR^5$ | H | 2.90 | 368 |
| 125 | F | F | O | H | —$CH_2CH_2$— | | H | H | Cl | $CF_3$ | $CR^5$ | H | 3.27 | 412 |
| 126 | Cl | F | O | H | —$CH_2CH_2$— | | H | H | Cl | $CF_3$ | $CR^5$ | H | 3.41 | 428 |
| 127 | F | F | O | H | H | H | H | H | Cl | H | $CR^5$ | H | 2.55 | 318 |
| 128 | Cl | F | O | H | H | H | H | H | Cl | H | $CR^5$ | H | 2.70 | 334 |
| 129 | F | F | O | H | Me | H | H | H | cyclohexyl | H | $CR^5$ | H | 4.34 | 380 |
| 130 | Cl | F | O | H | —$[CH_2]_4$— | | H | H | OEt | H | $CR^5$ | H | 3.59 | 398 |
| 131 | F | F | O | H | —$[CH_2]_4$— | | H | H | OEt | H | $CR^5$ | H | 3.44 | 382 |
| 132 | Cl | F | O | H | —$[CH_2]_4$— | | H | H | OMe | H | $CR^5$ | H | 3.19 | 384 |
| 133 | F | F | O | H | —$[CH_2]_4$— | | H | H | OMe | H | $CR^5$ | H | 3.06 | 368 |
| 134 | F | F | O | H | H | H | H | H | OMe | H | $CR^5$ | H | 2.08 | 314 |
| 135 | F | F | O | H | H | H | H | H | t-Bu [(1)] | H | $CR^5$ | H | 3.42 | 340 |
| 136 | Cl | F | O | H | H | H | H | H | t-Bu | H | $CR^5$ | H | 3.58 | 356 |
| 137 | Cl | F | O | H | H | —$CH_2CH_2$— | | H | H | H | $CR^5$ | H | 2.73 | 326 |
| 138 | F | F | O | H | H | —$CH_2CH_2$— | | H | H | H | $CR^5$ | H | 2.57 | 310 |
| 139 | Cl | F | O | H | H | —$CH_2CH_2CH_2CH_2$— | | H | H | H | $CR^5$ | H | 3.02 | 340 |
| 140 | F | F | O | H | H | —$CH_2CH_2CH_2CH_2$— | | H | H | H | $CR^5$ | H | 2.84 | 324 |
| 141 | F | F | O | Me | H | —$CH_2CH_2CH_2CH_2$— | | H | H | H | $CR^5$ | H | 2.92 | 338 |
| 142 | Cl | F | O | Me | H | —$CH_2CH_2CH_2CH_2$— | | H | H | H | $CR^5$ | H | 3.09 | 354 |
| 143 | Cl | F | O | H | H | H | phenoxy | H | H | H | $CR^5$ | H | 3.46 | 392 |
| 144 | F | F | O | H | H | H | phenoxy | H | H | H | $CR^5$ | H | 3.25 | 376 |
| 145 | F | F | O | H | H | H | H | phenoxy | H | H | $CR^5$ | H | 3.23 | 376 |
| 146 | Cl | F | O | H | H | H | H | phenoxy | H | H | $CR^5$ | H | 3.46 | 392 |
| 147 | Cl | F | O | 3-oxetanyl | H | H | H | phenoxy | H | H | $CR^5$ | H | 3.19 | 448 |
| 148 | F | F | O | 3-oxetanyl | H | H | H | phenoxy | H | H | $CR^5$ | H | 3.06 | 432 |
| 149 | Cl | F | O | Me | H | H | H | phenoxy | H | H | $CR^5$ | H | 3.46 | 406 |
| 150 | F | F | O | Me | H | H | H | phenoxy | H | H | $CR^5$ | H | 3.31 | 390 |
| 151 | Cl | F | O | H | H | H | H | H | phenoxy | H | $CR^5$ | H | 3.37 | 392 |
| 152 | F | F | O | H | H | H | H | H | phenoxy | H | $CR^5$ | H | 3.23 | 376 |
| 153 | Cl | F | O | Me | Me | H | H | H | phenoxy | H | $CR^5$ | H | 3.76 | 420 |
| 154 | F | F | O | Me | Me | H | H | H | phenoxy | H | $CR^5$ | H | 3.59 | 404 |
| 155 | Cl | F | O | Me | H | H | H | H | phenoxy | H | $CR^5$ | H | 3.48 | 406 |
| 156 | F | F | O | Me | H | H | H | H | phenoxy | H | $CR^5$ | H | 3.33 | 390 |
| 157 | Cl | F | O | Me | H | H | H | H | 4-chloro phenoxy | H | $CR^5$ | H | 3.96 | 440 |
| 158 | F | F | O | Me | H | H | H | H | 4-chloro phenoxy | H | $CR^5$ | H | 3.81 | 424 |
| 159 | Cl | F | O | H | Me | H | H | H | benzyloxy | H | $CR^5$ | H | 3.58 | 420 |
| 160 | Cl | F | O | H | H | H | H | H | benzyloxy | H | $CR^5$ | H | 3.37 | 406 |
| 161 | F | F | O | H | H | H | H | H | benzyloxy | H | $CR^5$ | H | 3.23 | 390 |
| 162 | F | F | O | H | Me | H | H | H | benzyloxy | H | $CR^5$ | H | 3.41 | 404 |
| 163 | F | F | O | H | H | H | phenyl | H | H | H | $CR^5$ | H | 3.21 | 360 |
| 164 | Cl | F | O | H | H | H | phenyl | H | H | H | $CR^5$ | H | 3.39 | 376 |
| 165 | Cl | F | O | H | H | H | H | phenyl | H | H | $CR^5$ | H | 3.33 | 376 |
| 166 | F | F | O | H | H | H | H | phenyl | H | H | $CR^5$ | H | 3.19 | 360 |
| 167 | Cl | F | O | H | Me | H | H | H | phenyl | H | $CR^5$ | H | 3.62 | 390 |
| 168 | Cl | F | O | H | H | H | H | H | phenyl | H | $CR^5$ | H | 3.35 | 376 |
| 169 | F | F | O | H | Me | H | H | H | phenyl | H | $CR^5$ | H | 3.46 | 374 |
| 170 | F | F | O | H | H | H | H | H | phenyl | H | $CR^5$ | H | 3.21 | 360 |
| 171 | Cl | F | O | H | —$[CH_2]_4$— | | H | H | H | H | N | — | 1.30 | 355 |
| 172 | F | F | O | H | —$[CH_2]_4$— | | H | H | H | H | N | — | 1.13 | 339 |
| 173 | Cl | F | O | Me | H | H | H | Cl | H | H | N | — | 2.01 | 349 |
| 174 | F | F | O | Me | H | H | H | Cl | H | H | N | — | 1.84 | 333 |
| 175 | F | F | O | H | Me | H | Cl | H | $CF_3$ | H | N | — | 3.19 | 401 |
| 176 | F | F | O | H | H | H | Cl | H | $CF_3$ | H | N | — | 2.76 | 387 |
| 177 | Cl | F | O | H | Me | H | Cl | H | $CF_3$ | H | N | — | 3.48 | 417 |
| 178 | Cl | F | O | H | H | H | Cl | H | $CF_3$ | H | N | — | 3.08 | 403 |
| 179 | F | F | O | Me | H | H | Cl | H | Cl | H | N | — | 2.53 | 367 |
| 180 | Cl | F | O | Me | H | H | Cl | H | Cl | H | N | — | 2.73 | 383 |
| 181 | F | F | O | OMe | H | H | Cl | H | Cl | H | N | — | 2.73 | 383 |
| 182 | Cl | F | O | OMe | H | H | Cl | H | Cl | H | N | — | 2.88 | 399 |
| 183 | F | F | O | cyclopentyl | H | H | Cl | H | Cl | H | N | — | 3.85 | 421 |
| 184 | Cl | F | O | cyclopentyl | H | H | Cl | H | Cl | H | N | — | 4.11 | 437 |
| 185 | F | F | O | Me | Me | H | Cl | H | Cl | H | N | — | 2.92 | 381 |
| 186 | Cl | F | O | Me | Me | H | Cl | H | Cl | H | N | — | 3.11 | 397 |
| 187 | F | F | O | cyclopentyl | Me | H | Cl | H | Cl | H | N | — | 4.44 | 435 |
| 188 | Cl | F | O | cyclopentyl | Me | H | Cl | H | Cl | H | N | — | 4.67 | 451 |
| 189 | Cl | F | O | cyclopentyl | H | H | Cl | H | $CF_3$ | H | N | — | 4.21 | 471 |
| 190 | F | F | O | cyclopentyl | H | H | Cl | H | $CF_3$ | H | N | — | 3.96 | 455 |
| 191 | Cl | F | O | H | Et | H | Cl | H | Cl | H | $CR^5$ | H | 3.79 | 396 |
| 192 | F | F | O | H | Et | H | Cl | H | Cl | H | $CR^5$ | H | 3.61 | 380 |

Note
[(1)] i-Pr: isopropyl; c-Pr: cyclopropyl; t-Bu: tertiobutyl

The following examples illustrate in a non limiting manner the preparation and efficacy of the compounds of formula (I) according to the invention.

Synthesis of 5-chloro-3-(difluoromethyl)-1-methyl-1H-pyrazole-4-carboxylic acid (example IIIa-1)

In a 500 ml flask, 6.0 g (31 mmol) of 5-chloro-3-(difluoromethyl)-1-methyl-1H-pyrazole-4-carbaldehyde are added to 30 ml of toluene. A solution of 2.4 g (62 mmol) of sodium hydroxide in 6 ml of water is added to the reaction mixture, followed by 103 ml of a 30% solution of hydrogen peroxide in water, whilst keeping the temperature below 37° C. After the end of the addition, the reaction mixture is stirred at 50° C. for 7 hours. Once the reaction mixture is back to room temperature, the two phases are separated and the organic phase is extracted with 100 ml of water. The combined aqueous phases are acidified to pH 2 with aqueous hydrochloric acid. The resulting white precipitate is filtered, washed twice with 20 ml of water, and dried to yield 3.2 g of 5-chloro-3-(difluoromethyl)-1-methyl-1H-pyrazole-4-carboxylic acid as a white solid. $^1$H NMR (400 MHz, DMSO-$d_6$) δ ppm: 3.78 (s, 3H); 7.12 (t, 1H, $J_{HF}$=53.60 Hz); 13.19 (s, 1H); IR (KBr): 1688 cm$^{-1}$ (C=O); 2200-3200 cm$^{-1}$ broad (hydrogen bond).

Synthesis of 5-chloro-3-(difluoromethyl)-1-methyl-1H-pyrazole-4-carbonyl chloride (example IIIb-1)

3.2 g of 5-chloro-3-(difluoromethyl)-1-methyl-1H-pyrazole-4-carboxylic acid and 44.3 ml of thionyl chloride are refluxed for 5 hours. After cooling down, the reaction mixture is evaporated under vacuum to yield 3.5 g of 5-chloro-3-(difluoromethyl)-1-methyl-1H-pyrazole-4-carbonyl chloride as a yellow oil. $^1$H NMR (400 MHz, CHCl$_3$-$d_6$) δ ppm: 3.97 (s, 3H); 7.00 (t, J=52.01 Hz, 1 H); IR (TQ): 1759 and 1725 cm$^{-1}$ (C=O).

Synthesis of 3-(difluoromethyl)-5-fluoro-1-methyl-1H-pyrazole-4-carbonyl fluoride (example IIIc-1)

To a dried solution of 4.0 g (70 mmol) of potassium fluoride in 21 ml of tetrahydrothiophene-1,1-dioxide is added a solution of 5.0 g (22 mmol) of 5-chloro-3-(difluoromethyl)-1-methyl-1H-pyrazole-4-carbonyl chloride in 15 ml of toluene at 100° C. The resulting reaction mixture is stirred at 190-200° C. for 22 hours. Distillation under vacuum yields 8 g of a solution (0.25 M) of 3-(difluoromethyl)-5-fluoro-1-methyl-1H-pyrazole-4-carbonyl fluoride in tetrahydrothiophene-1,1-dioxide. $^1$H NMR (250 MHz, CHCl$_3$-$d_6$) δ ppm: 3.87 (s, 3H); 6.79 (t, J=53.75 Hz, 1 H); $^{19}$F NMR (250 MHz, CHCl$_3$-$d_6$) δ ppm: 45.37 (s, COF); −117.5 (d, J=28.2 Hz); −131.6 (m).

Synthesis of 3-(difluoromethyl)-5-fluoro-1-methyl-1H-pyrazole-4-carboxylic acid (example IIId-1)

To 400 ml of a 1N sodium hydroxide aqueous solution, is added dropwise 67.5 g of a solution (0.1 M) of 3-(difluoromethyl)-5-fluoro-1-methyl-1H-pyrazole-4-carbonyl fluoride in tetrahydro-thiophene-1,1-dioxide. The temperature is kept below 20° C. during the addition. After 2 hours of stirring at room temperature, the reaction mixture is carefully acidified to pH 2 with concentrated aqueous hydrochloric acid. The resulting white precipitate is filtered, washed with water, and dried to yield 6 g of 3-(difluoromethyl)-5-fluoro-1-methyl-1H-pyrazole-4-carboxylic acid as a white solid. $^1$H NMR (400 MHz, DMSO-$d_6$) δ ppm: 3.90 (s, 3H); 7.22 (t, 1H, $J_{HF}$=53.55 Hz); 13.33 (s, 1H).

Synthesis of 3-(difluoromethyl)-5-fluoro-1-methyl-1H-pyrazole-4-carbonyl chloride (example IIIe-1)

9.1 g of 3-(difluoromethyl)-5-fluoro-1-methyl-1H-pyrazole-4-carboxylic acid and 75.5 ml of thionyl chloride are refluxed for 1.5 hours. After cooling down, the reaction mixture is evaporated under vacuum to yield 10 g of 3-(difluoromethyl)-5-fluoro-1-methyl-1H-pyrazole-4-carbonyl chloride as a yellow oil. GC-MS; observed m/z: Molecular ion: (M$^+$)=212; fragments: (M$^+$.-Cl)=177 and (M$^+$.-F)=193.

GENERAL PREPARATION EXAMPLE 2

Preparation of Amide of Formula (I) on Chemspeed™ Apparatus

In a 13 ml Chemspeed™ vial is distributed 4 ml of a 0.15 M solution of the amine (II) (0.60 mmol) in dichloromethane followed by 0.72 mmol of triethylamine. At a rate of 1 ml/mn, 2 ml of a 0.30 M solution of the acyl chloride (IIIb) or (IIIe) (0.60 mmol) are added and the mixture is then stirred at room temperature overnight. 1 ml of water is then added and the mixture is poured over a basic alumina cartridge (2 g) and eluted with dichloromethane. The solvents are removed and the crude amide derivative is analyzed by LCMS and NMR. Insufficiently pure compounds are further purified by preparative LCMS.

GENERAL PREPARATION EXAMPLE 3

Thionation of Amide of Formula (I) on Chemspeed™ Apparatus

In a 13 ml Chemspeed™ vial is weighted 0.27 mmol of phosphorous pentasulfide ($P_2S_5$). 3 ml of a 0.18 M solution of the amide (I) (0.54 mmol) in dioxane are added and the mixture is heated at reflux for two hours. The temperature is then cooled to 80° C. and 2.5 ml of water are added. The mixture is heated at 80° C. for one more hour. 2 ml of water are then added and the reaction mixture is extracted twice by 4 ml of dichloromethane. The organic phase is deposited on a basic alumina cartridge (2 g) and eluted twice by 8 ml of dichloromethane. The solvents are removed and the crude thioamide derivative is analyzed by LCMS and NMR. Insufficiently pure compounds are further purified by preparative LCMS.

EXAMPLE A

In Vivo Preventive Test on *Sphaerotheca fuliginea* (Cucumber)

Solvent: 49 parts by weight of N,N-dimethylformamide
Emulsifier: 1 part by weight of alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. After the spray coating has dried on, the plants are inoculated with an aqueous spore suspension of *Sphaerotheca fuliginea*. The plants are then placed in a greenhouse at approximately 23° C. and a relative atmospheric humidity of approximately 70%.

The test is evaluated 7 days after the inoculation. 0% means an efficacy which corresponds to that of the untreated control, while an efficacy of 100% means that no disease is observed. Under these conditions, good (at least 75% of disease control) to total protection (100% of disease control) is observed at a dose of 500 ppm ppm of active ingredient with the following compounds from table A:

TABLE A

| Example | Efficacy |
| --- | --- |
| 12 | 95 |
| 13 | 90 |
| 15 | 83 |
| 17 | 94 |
| 18 | 90 |
| 19 | 84 |
| 20 | 94 |
| 22 | 80 |
| 24 | 89 |
| 26 | 88 |
| 28 | 85 |
| 29 | 93 |
| 32 | 95 |
| 33 | 96 |
| 35 | 86 |
| 36 | 93 |
| 38 | 89 |
| 39 | 95 |
| 40 | 83 |
| 45 | 100 |
| 49 | 94 |
| 50 | 98 |
| 52 | 80 |
| 53 | 95 |
| 55 | 83 |
| 56 | 95 |
| 65 | 85 |
| 68 | 100 |
| 70 | 100 |
| 71 | 91 |
| 72 | 98 |
| 73 | 98 |
| 74 | 95 |
| 75 | 100 |
| 76 | 93 |
| 78 | 93 |
| 82 | 94 |
| 84 | 90 |
| 90 | 100 |
| 91 | 95 |
| 98 | 96 |
| 99 | 95 |
| 103 | 91 |
| 108 | 85 |
| 112 | 95 |
| 116 | 75 |
| 117 | 95 |
| 118 | 95 |
| 125 | 100 |
| 162 | 88 |
| 169 | 89 |
| 175 | 95 |
| 177 | 93 |
| 191 | 100 |
| 192 | 100 |

Under the same conditions, high (at least 90%) protection at a dose of 500 ppm of active ingredient with compound 29, whereas medium (less than 60%) protection is observed with the compound of example 1.043 disclosed in patent application WO-2009/024342 as in table A2.

TABLE A2

| Example | dose (ppm) | Efficacy |
| --- | --- | --- |
| 29 from this invention | 500 | 93 |
| 1.043 from WO2009/024342 | 500 | 55 |

Example 1.043 disclosed in international patent WO-2009/024342 corresponds to N-[1-(2,3-dichlorophenyl)ethyl]-3-(difluoromethyl)-1-methyl-1H-pyrazole-4-carboxamide.

These results show that the compounds according to the invention have a better biological activity than the structurally closest compounds disclosed in WO-2009/024342.

EXAMPLE B

In Vivo Preventive Test on *Alternaria Solani*
(Tomato)

Solvent: 49 parts by weight of N,N-dimethylformamide
Emulsifier: 1 part by weight of alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Alternaria solani*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the untreated control while an efficacy of 100% means that no disease is observed.

Under these conditions, good (at least 70% of disease control) to total protection (100% of disease control) is observed at a dose of 500 ppm of active ingredient with the following compounds from table B:

TABLE B

| Example | Efficacy |
| --- | --- |
| 1 | 95 |
| 2 | 93 |
| 12 | 90 |
| 13 | 95 |
| 15 | 95 |
| 16 | 80 |
| 17 | 80 |
| 18 | 95 |
| 19 | 90 |
| 20 | 95 |
| 23 | 89 |
| 24 | 94 |
| 26 | 94 |
| 27 | 80 |
| 28 | 95 |
| 29 | 94 |
| 30 | 90 |
| 33 | 95 |
| 36 | 94 |
| 37 | 94 |
| 38 | 94 |
| 39 | 70 |
| 40 | 94 |
| 41 | 80 |
| 43 | 90 |
| 44 | 100 |

TABLE B-continued

| Example | Efficacy |
|---|---|
| 45 | 100 |
| 46 | 100 |
| 50 | 95 |
| 51 | 94 |
| 53 | 94 |
| 54 | 89 |
| 55 | 95 |
| 56 | 100 |
| 65 | 90 |
| 68 | 80 |
| 70 | 90 |
| 71 | 95 |
| 72 | 95 |
| 73 | 95 |
| 74 | 95 |
| 76 | 94 |
| 78 | 100 |
| 81 | 90 |
| 82 | 100 |
| 83 | 90 |
| 84 | 100 |
| 85 | 95 |
| 88 | 80 |
| 89 | 95 |
| 90 | 95 |
| 91 | 100 |
| 98 | 70 |
| 99 | 95 |
| 100 | 80 |
| 101 | 70 |
| 103 | 90 |
| 105 | 95 |
| 107 | 80 |
| 110 | 94 |
| 112 | 80 |
| 113 | 90 |
| 115 | 94 |
| 116 | 95 |
| 117 | 100 |
| 118 | 100 |
| 121 | 70 |
| 127 | 90 |
| 129 | 95 |
| 137 | 89 |
| 138 | 94 |
| 139 | 100 |
| 140 | 94 |
| 141 | 80 |
| 144 | 89 |
| 145 | 90 |
| 147 | 70 |
| 148 | 80 |
| 150 | 70 |
| 152 | 89 |
| 153 | 90 |
| 154 | 95 |
| 156 | 89 |
| 158 | 95 |
| 161 | 94 |
| 162 | 100 |
| 166 | 78 |
| 167 | 95 |
| 169 | 94 |
| 170 | 94 |
| 175 | 95 |
| 176 | 70 |
| 177 | 90 |
| 179 | 90 |
| 180 | 80 |
| 181 | 80 |
| 185 | 100 |
| 191 | 95 |
| 192 | 95 |

Under the same conditions, excellent (at least 95%) protection to high (at least 90%) protection is observed at a dose of 500 ppm and 100 ppm of active ingredient with compound 129, whereas good (at least 80%) protection to no protection is observed with the compound of example 1.029 disclosed in patent application WO-2009/024342 as in table B2.

TABLE B2

| Example | dose (ppm) | Efficacy |
|---|---|---|
| 129 from this invention | 500 | 95 |
|  | 100 | 90 |
| 1.029 from WO2009/024342 | 500 | 89 |
|  | 100 | 0 |

Example 1.029 disclosed in international patent WO-2009/024342 corresponds to N-[1-(4-cyclohexylphenyl)ethyl]-3-(difluoromethyl)-1-methyl-1H-pyrazole-4-carboxamide.

These results show that the compounds according to the invention have a better biological activity than the structurally closest compounds disclosed in WO-2009/024342.

Under the same conditions, high (at least 90%) protection to excellent (at least 95%) protection is observed at a dose of 500 ppm active ingredient with compound 28 and compound 30 without any plant damages, whereas 100% of plant damages is observed with the compound of example 89 disclosed in patent application WO-2009/016221 as in table B3.

TABLE B3

| Example | dose (ppm) | Efficacy |
|---|---|---|
| 28 from this invention | 500 | 95 |
| 30 from this invention | 500 | 90 |
| 89 from WO2009/016221 | 500 | —[a] | note
[a] 100% of plant damages

Example 89 disclosed in international patent WO-2009/016221 corresponds to N-cyclopropyl-3-(difluoromethyl)-5-fluoro-1-methyl-N-[1-(1-naphthyl)ethyl]-1H-pyrazole-4-carboxamide.

These results show that the compounds according to the invention have a better biological activity than the structurally closest compounds disclosed in WO-2009/016221.

Under the same conditions, high (at least 90%) protection to total protection is observed at a dose of 500 ppm active ingredient with compound 43 and compound 45 without any plant damages, whereas poor (less than 30%) protection to 90% of plant damages is observed with the compounds of example 236 and example 263 disclosed in patent application WO-2007/087906 as in table B4.

TABLE B4

| Example | dose (ppm) | Efficacy |
|---|---|---|
| 43 from this invention | 500 | 90 |
| 45 from this invention | 500 | 100 |
| 236 from WO2007/087906 | 500 | 30 |
| 263 from WO2007/087906 | 500 | —[b] | note
[b] 90% of plant damages

Example 236 disclosed in international patent WO-2007/087906 corresponds to N-cyclopropyl-N-(2,4-dichlorobenzyl)-5-fluoro-1,3-dimethyl-1H-pyrazole-4-carboxamide and example 263 disclosed in international patent WO-2007/087906 corresponds to N-cyclopropyl-N-[1-(2,4-dichlorophenyl)ethyl]-5-fluoro-1,3-dimethyl-1H-pyrazole-4-carboxamide.

These results show that the compounds according to the invention have a better biological activity than the structurally closest compounds disclosed in WO-2007/087906.

EXAMPLE C

In Vivo Preventive Test on *Pyrenophora teres* (Barley)

Solvent: 49 parts by weight of N,N-dimethylacetamid
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Pyrenophora teres*. The plants remain for 48 hours in an incubation cabinet at 22° C. and a relative atmospheric humidity of 100%. Then the plants are placed in a greenhouse at a temperature of approximately 20° C. and a relative atmospheric humidity of approximately 80%.

The test is evaluated 7-9 days after the inoculation. 0% means an efficacy which corresponds to that of the untreated control while an efficacy of 100% means that no disease is observed.

Under these conditions, good (at least 70% of disease control) to total protection (100% of disease control) is observed at a dose of 500 ppm of active ingredient with the following compounds from table C:

TABLE C

| Example | Efficacy |
|---|---|
| 1 | 95 |
| 2 | 94 |
| 5 | 89 |
| 6 | 78 |
| 12 | 100 |
| 13 | 95 |
| 15 | 95 |
| 16 | 100 |
| 17 | 100 |
| 18 | 100 |
| 20 | 95 |
| 24 | 100 |
| 27 | 100 |
| 28 | 100 |
| 29 | 100 |
| 30 | 100 |
| 31 | 100 |
| 33 | 100 |
| 36 | 100 |
| 38 | 95 |
| 39 | 95 |
| 40 | 95 |
| 43 | 100 |
| 44 | 100 |
| 45 | 100 |
| 46 | 100 |
| 50 | 95 |
| 51 | 80 |
| 53 | 95 |
| 55 | 100 |
| 56 | 100 |
| 61 | 100 |
| 62 | 100 |
| 64 | 95 |
| 65 | 94 |
| 67 | 90 |
| 68 | 100 |
| 70 | 100 |
| 71 | 95 |
| 72 | 100 |
| 73 | 100 |
| 74 | 100 |
| 75 | 100 |
| 78 | 100 |
| 79 | 95 |
| 80 | 100 |
| 82 | 95 |
| 84 | 100 |
| 85 | 100 |
| 87 | 95 |
| 89 | 100 |
| 90 | 100 |
| 91 | 95 |
| 92 | 70 |
| 93 | 95 |
| 94 | 80 |
| 99 | 95 |
| 101 | 80 |
| 103 | 70 |
| 104 | 78 |
| 105 | 94 |
| 106 | 90 |
| 107 | 100 |
| 108 | 94 |
| 110 | 80 |
| 112 | 95 |
| 113 | 80 |
| 115 | 90 |
| 116 | 100 |
| 117 | 100 |
| 118 | 100 |
| 121 | 94 |
| 123 | 70 |
| 125 | 95 |
| 126 | 95 |
| 127 | 90 |
| 128 | 80 |
| 129 | 100 |
| 131 | 94 |
| 133 | 95 |
| 135 | 95 |
| 139 | 70 |
| 140 | 80 |
| 141 | 100 |
| 142 | 95 |
| 148 | 95 |
| 149 | 70 |
| 150 | 100 |
| 152 | 95 |
| 153 | 80 |
| 154 | 100 |
| 156 | 90 |
| 157 | 90 |
| 158 | 100 |
| 159 | 95 |
| 161 | 90 |
| 162 | 100 |
| 166 | 80 |
| 167 | 90 |
| 169 | 100 |
| 170 | 95 |
| 174 | 75 |
| 175 | 100 |
| 177 | 100 |
| 179 | 100 |
| 180 | 100 |
| 181 | 100 |
| 182 | 95 |
| 185 | 95 |
| 187 | 90 |
| 188 | 95 |
| 191 | 100 |
| 192 | 100 |

Under the same conditions, good (at least 70%) protection and excellent (at least 95%) protection is observed at a dose of 500 ppm of active ingredient with compound 123 and compound 135, whereas no protection or poor (less than 30%) protection is observed with the compounds of example 145 and example 146 disclosed in patent application CN1188764 as in table C2.

TABLE C2

| Example | dose (ppm) | Efficacy |
| --- | --- | --- |
| 123 from this invention | 500 | 70 |
| 135 from this invention | 500 | 95 |
| 145 from CN1188764 | 500 | 0 |
| 146 from CN1188764 | 500 | 20 |

Example 145 disclosed in international patent CN1188764 corresponds to 5-chloro-1,3-dimethyl-N-[4-(trifluoromethyl)benzyl]-1H-pyrazole-4-carboxamide and example 146 disclosed in international patent CN1188764 corresponds to N-(4-tert-butylbenzyl)-5-chloro-1,3-dimethyl-1H-pyrazole-4-carboxamide.

These results show that the compounds according to the invention have a better biological activity than the structurally closest compounds disclosed in CN1188764.

Under the same conditions, high (at least 80%) protection is observed at a dose of 500 ppm of active ingredient with compound 127 and compound 128, whereas no protection is observed with the compound of example 24 disclosed in J. Korean Agric. Chem. Soc. (1992), 35(2), 87-91 as in table C3.

TABLE C3

| Example | dose (ppm) | Efficacy |
| --- | --- | --- |
| 127 from this invention | 500 | 90 |
| 128 from this invention | 500 | 80 |
| 24 from J. Korean. Agric. Chem. Soc (1992), 35, 87 | 500 | 0 |

Example 24 disclosed in J. Korean Agric. Chem. Soc. (1992), 35(2), 87-91 corresponds to 5-chloro-N-(4-chlorobenzyl)-1,3-dimethyl-1H-pyrazole-4-carboxamide These results show that the compounds according to the invention have a better biological activity than the structurally closest compounds disclosed in J. Korean Agric. Chem. Soc. (1992), 35(2), 87-91.

EXAMPLE D

In Vivo Preventive Test on *Leptosphaeria nodorum* (Wheat)

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for preventive activity, young plants are sprayed with a preparation of active compound at the stated rate of application. One day after this treatment, the plants are inoculated with an aqueous spore suspension of *Leptosphaeria nodorum*. The plants remain for 48 hours in an incubation cabinet at 22° C. and a relative atmospheric humidity of 100%. Then the plants are placed in a greenhouse at a temperature of approximately 22° C. and a relative atmospheric humidity of approximately 90%.

The test is evaluated 7-9 days after the inoculation. 0% means an efficacy which corresponds to that of the untreated control, while an efficacy of 100% means that no disease is observed.

Under these conditions, good (at least 70%) to excellent protection (at least 95%) is observed at a dose of 500 ppm of active ingredient with the following compounds from table D:

TABLE D

| Example | Efficacy |
| --- | --- |
| 18 | 95 |
| 30 | 90 |
| 31 | 80 |
| 39 | 90 |
| 44 | 89 |
| 45 | 95 |
| 56 | 70 |
| 72 | 78 |
| 74 | 80 |
| 76 | 89 |
| 79 | 94 |
| 117 | 70 |
| 118 | 70 |
| 135 | 75 |
| 136 | 70 |
| 141 | 95 |
| 154 | 70 |
| 179 | 70 |
| 181 | 70 |
| 185 | 95 |
| 187 | 80 |

EXAMPLE E

In Vivo Preventive Test on *Puccinia triticina* (Wheat)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Puccinia triticina*. The plants remain for 48 hours in an incubation cabinet at approximately 20° C. and a relative atmospheric humidity of approximately 100%.

The plants are placed in the greenhouse at a temperature of approximately 20° C. and a relative atmospheric humidity of approximately 80%.

The test is evaluated 8 days after the inoculation. 0% means an efficacy which corresponds to that of the untreated control, while an efficacy of 100% means that no disease is observed.

Under these conditions, good (at least 70%) to total protection is observed at a dose of 500 ppm of active ingredient with the following compounds from table E:

TABLE E

| Example | Efficacy |
| --- | --- |
| 29 | 80 |
| 68 | 70 |
| 90 | 95 |

TABLE E-continued

| Example | Efficacy |
|---|---|
| 98 | 95 |
| 99 | 100 |
| 100 | 80 |
| 101 | 90 |
| 106 | 80 |
| 117 | 70 |
| 126 | 78 |
| 141 | 95 |
| 180 | 80 |
| 181 | 70 |
| 184 | 70 |
| 185 | 90 |

Under the same conditions, good (at least 80%) protection at a dose of 500 ppm of active ingredient with compound 29, whereas no protection is observed with the compound of example 1.043 disclosed in patent application WO-2009/024342 as in table E2.

TABLE E2

| Example | dose (ppm) | Efficacy |
|---|---|---|
| 29 from this invention | 500 | 80 |
| 1.043 from WO2009/024342 | 500 | 0 |

Example 1.043 disclosed in international patent WO-2009/024342 corresponds to N-[1-(2,3-dichlorophenyl)ethyl]-3-(difluoromethyl)-1-methyl-1H-pyrazole-4-carboxamide.

These results show that the compounds according to the invention have a better biological activity than the structurally closest compounds disclosed in WO-2009/024342.

EXAMPLE F

In Vivo Preventive Test on *Septoria tritici* (Wheat)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are sprayed with a spore suspension of *Septoria tritici*. The plants remain for 48 hours in an incubation cabinet at approximately 20° C. and a relative atmospheric humidity of approximately 100% and afterwards for 60 hours at approximately 15° C. in a translucent incubation cabinet at a relative atmospheric humidity of approximately 100%.

The plants are placed in the greenhouse at a temperature of approximately 15° C. and a relative atmospheric humidity of approximately 80%.

The test is evaluated 21 days after the inoculation. 0% means an efficacy which corresponds to that of the untreated control, while an efficacy of 100% means that no disease is observed.

Under these conditions, good (at least 70%) to total protection is observed at a dose of 500 ppm of active ingredient with the following compounds from table F:

TABLE F

| Example | Efficacy |
|---|---|
| 29 | 88 |
| 68 | 100 |
| 72 | 90 |
| 90 | 100 |
| 141 | 70 |
| 185 | 100 |

EXAMPLE G

In Vivo Preventive Test on *Blumeria graminis* (Barley)

Solvent: 49 parts by weight of N,N-dimethylacetamide
Emulsifier: 1 part by weight of alkylaryl polyglycol ether To produce a suitable preparation of active compound, 1 part by weight of active compound or active compound combination is mixed with the stated amounts of solvent and emulsifier, and the concentrate is diluted with water to the desired concentration.

To test for preventive activity, young plants are sprayed with the preparation of active compound or active compound combination at the stated rate of application.

After the spray coating has been dried, the plants are dusted with spores of *Blumeria graminis* f.sp. *hordei*.

The plants are placed in the greenhouse at a temperature of approximately 18° C. and a relative atmospheric humidity of approximately 80% to promote the development of mildew pustules.

The test is evaluated 7 days after the inoculation. 0% means an efficacy which corresponds to that of the untreated control, while an efficacy of 100% means that no disease is observed.

Under these conditions, total protection is observed at a dose of 500 ppm of active ingredient with the following compounds from table G:

TABLE G

| Example | Efficacy |
|---|---|
| 68 | 100 |
| 72 | 100 |
| 90 | 100 |
| 141 | 100 |
| 185 | 100 |

The invention claimed is:
1. A compound of formula (I)

$$\text{(I)}$$

[Chemical structure showing a pyrazole ring with H$_3$C-N, N, X$^2$, X$^2$, H substituents connected via a C(=T) group to N-Z$^1$, with X$^1$, R$^4$, Y, R$^3$, R$^2$, Z$^2$, Z$^3$, R$^1$ substituents on a phenyl ring]

wherein
Y represents CR$^5$ or N;
T represents O or S;

$X^1$ and $X^2$ which can be the same or different, represent a chlorine or a fluorine atom;

$Z^1$ represents a hydrogen atom, substituted or non substituted $C_1$-$C_8$-alkyl; substituted or non substituted $C_1$-$C_8$-alkoxy; substituted or non substituted $C_2$-$C_8$-alkenyl; substituted or non substituted $C_2$-$C_8$-alkynyl; substituted or non substituted $C_4$-$C_7$-cycloalkyl; substituted or non substituted $C_3$-$C_7$-cycloalkyl-$C_1$-$C_8$-alkyl; substituted or non substituted 3-oxetanyl; or substituted or non substituted 3-thietanyl;

$Z^2$ and $Z^3$, which can be the same or different, represent a hydrogen atom; substituted or non substituted $C_1$-$C_8$-alkyl; substituted or non substituted $C_2$-$C_8$-alkenyl; substituted or non substituted $C_2$-$C_8$-alkynyl; cyano; isonitrile; nitro; a halogen atom; substituted or non substituted $C_1$-$C_8$-alkoxy; substituted or non substituted $C_2$-$C_8$-alkenyloxy; substituted or non substituted $C_2$-$C_8$-alkynyloxy; substituted or non substituted $C_3$-$C_7$-cycloalkyl; substituted or non substituted $C_1$-$C_8$-alkylsulfanyl; substituted or non substituted $C_1$-$C_8$-alkylsulfonyl; substituted or non substituted $C_1$-$C_8$alkylsulfinyl; amino; substituted or non substituted $C_1$-$C_8$-alkylamino; substituted or non substituted di-$C_1$-$C_8$-alkylamino; substituted or non substituted $C_1$-$C_8$-alkoxycarbonyl; substituted or non substituted $C_1$-$C_8$-alkylcarbamoyl; substituted or non substituted di-$C_1$-$C_8$-alkylcarbamoyl; or substituted or non substituted N-$C_1$-$C_8$-alkyl-$C_1$-$C_8$-alkoxy-carbamoyl; or $Z^3$ and $R^1$ together with the consecutive carbon atoms to which they are linked form a substituted or non substituted 5-, 6- or 7-membered, partly saturated, carbo- or hetero-cycle comprising up to 3 heteroatoms and $Z^2$ is as herein described; or $Z^2$ and $Z^3$ together with the carbon atom to which they are linked form a substituted or non substituted $C_3$-$C_7$ cycloalkyl;

$R^1$, $R^2$, $R^3$, $R^4$ and $R^5$, which can be the same or different, represent a hydrogen atom;

a halogen atom; nitro; cyano; isonitrile; hydroxyl; sulfanyl; amino; pentafluoro-$\lambda^6$-sulfanyl; substituted or non substituted $C_1$-$C_8$-alkyl; $C$-$C_8$-halogenoalkyl comprising up to 9 halogen atoms which can be the same or different; substituted or non substituted $C_1$-$C_8$-alkylamino; substituted or non substituted di-$C_1$-$C_8$-alkylamino ; substituted or non substituted $C_1$-$C_8$-alkoxy; $C_1$-$C_8$-halogenoalkoxy comprising up to 9 halogen atoms which can be the same or different; $C_1$-$C_8$-alkoxy-$C_1$-$C_8$-alkyl; substituted or non substituted $C_1$-$C_8$-alkylsulfanyl; $C_1$-$C_8$-halogenoalkylsulfanyl comprising up to 9 halogen atoms which can be the same or different; substituted or non substituted $C_2$-$C_8$-alkenyl; $C_2$-$C_8$-halogenoalkenyl comprising up to 9 halogen atoms which can be the same or different; substituted or non substituted $C_2$-$C_8$-alkynyl; $C_2$-$C_8$-halogenoalkynyl comprising up to 9 halogen atoms which can be the same or different; substituted or non substituted $C_2$-$C_8$-alkenyloxy; $C_2$-$C_8$-halogenoalkenyloxy comprising up to 9 halogen atoms which can be the same or different; substituted or non substituted $C_2$-$C_8$-alkynyloxy; $C_2$-$C_8$-halogenoalkynyloxy comprising up to 9 halogen atoms which can be the same or different; substituted or non substituted $C_3$-$C_7$-cycloalkyl; $C_3$-$C_7$-halogenocycloalkyl comprising up to 9 halogen atoms which can be the same or different; substituted or non substituted $C_3$-$C_7$-cycloalkyl-$C_1$-$C_8$-alkyl; substituted or non substituted $C_3$-$C_7$-cycloalkyl-$C_2$-$C_8$-alkenyl; substituted or non substituted $C_3$-$C_7$-cycloalkyl-$C_2$-$C_8$-alkynyl; substituted or non substituted $C_3$-$C_7$-cycloalkyl-$C_3$-$C_7$-cycloalkyl; substituted or non substituted $C_1$-$C_8$-alkyl-$C_3$-$C_7$-cycloalkyl; formyl; formyloxy; formylamino; carboxy; carbamoyl; N-hydroxycarbamoyl; carbamate; (hydroxyimino)-$C_1$-$C_8$-alkyl; substituted or non substituted $C_1$-$C_8$-alkylcarbonyl; $C_1$-$C_8$-halogenoalkylcarbonyl comprising up to 9 halogen atoms which can be the same or different; substituted or non substituted $C_1$-$C_8$-alkylcarbamoyl; substituted or non substituted di-$C_1$-$C_8$-alkylcarbamoyl; N-(substituted or non substituted $C_1$-$C_8$-alkyloxy)carbamoyl; substituted or non substituted $C_1$-$C_8$-alkoxycarbamoyl; N -(substituted or non substituted $C_1$-$C_8$-alkyl)-(substituted or non substituted $C_1$-$C_8$-alkoxy)-carbamoyl; substituted or non substituted $C_1$-$C_8$-alkoxycarbonyl; $C_1$-$C_8$-halogenoalkoxycarbonyl comprising up to 9 halogen atoms which can be the same or different; substituted or non substituted $C_1$-$C_8$-alkylaminocarbonyl; di- substituted or non substituted $C_1$-$C_8$-alkylaminocarbonyl; substituted or non substituted $C_1$-$C_8$-alkylcarbonyloxy; $C_1$-$C_8$-halogenoalkylcarbonyloxy comprising up to 9 halogen atoms which can be the same or different; substituted or non substituted $C_1$-$C_8$-alkylcarbonylamino; $C_1$-$C_8$-halogenoalkylcarbonylamino comprising up to 9 halogen atoms which can be the same or different; substituted or non substituted $C_1$-$C_8$-alkylaminocarbonyloxy; substituted or non substituted di-$C_1$-$C_8$-alkylaminocarbonyloxy; substituted or non substituted $C_1$-$C_8$-alkyloxycarbonyloxy; substituted or non substituted $C_1$-$C_8$-alkylsulfinyl; $C_1$-$C_8$-halogenoalkylsulfinyl comprising up to 9 halogen atoms which can be the same or different; substituted or non substituted $C_1$-$C_8$-alkylsulfonyl; $C_1$-$C_8$-halogenoalkylsulfonyl comprising up to 9 halogen atoms which can be the same or different; substituted or non substituted $C_1$-$C_8$-alkoxyimino; ($C_1$-$C_8$-alkoxyimino)-$C_1$-$C_8$-alkyl; substituted or non substituted ($C_1$-$C_8$-alkenyloxyimino)-C -$C_8$-alkyl; ($C_I$-$C_8$-alkynyloxyim ino)-$C_1$-$C_8$-alkyl; a (benzyloxyimino)-$C_1$-$C_8$-alkyl; tri(substituted or non substituted $C_I$-$C_8$-alkyOsilyl; tri(substituted or non substituted $C_1$-$C_8$-alkyl)silyl-$C_1$-$C_8$-alkyl; benzyloxy which can be substituted by up to 5 groups Q; benzylsulfanyl which can be substituted by up to 5 groups Q; benzylamino which can be substituted by up to 5 groups Q; aryloxy which can be substituted by up to 7 groups Q; arylamino which can be substituted by up to 7 groups Q; arylsulfanyl which can be substituted by up to 7 groups Q; aryl-$C_1$-$C_8$alkyl which can be substituted by up to 7 groups Q; aryl-$C_2$-$C_8$-alkenyl which can be substituted by up to 7 groups Q; aryl-$C_2$-$C_8$-alkynyl which can be sub.stituted by up to 7 groups Q; pyridinyl which can be substituted by up to 4 groups Q; pyridinyloxy which can be substituted by up to 4 groups Q; aryl-$C_3$-$C_7$-cycloalkyl which can be substituted by up to 7 groups Q; or two vicinal substituents R together with the consecutive carbon atoms to which they are linked form a substituted or non substituted 5- or 6-membered, saturated, carbo- or hetero-cycle comprising up to 3 heteroatoms and the other substituents R are as herein-described; or $R^1$ and $Z^3$ together with the consecutive carbon atoms to which they are linked form a substituted or non substituted 5-, 6- or 7-membered, partly saturated, carbo- or hetero-cycle comprising up to 3 heteroatoms, and $R^2$ to $R^5$ are as herein-described;

Q, which can be the same or different, represents a halogen atom; cyano; nitro; $C_1$-$C_8$-alkyl; $C_1$-$C_8$alkoxy; $C_1$-$C_8$-alkylsulfanyl; $C_1$-$C_8$-halogenoalkyl comprising up to 9 halogen atoms which can be the same or different; $C_1$-$C_8$-halogenoalkoxy comprising up to 9 halogen atoms which can be the same or different; tri($C_1$-$C_8$)alkylsilyl or tri($C_1$-$C_8$)alkylsilyl-$C_1$-$C_8$-alkyl;

as well as salts, N-oxides, metal complexes, metalloid complexes and optically active or geometric isomers thereof.

2. A compound according to claim 1 wherein Y represents $CR^5$.

3. A compound according to claim 1 wherein Y represents N.

4. A compound according to claim 1 wherein T represents O.

5. A compound according to claim 1 wherein $X^1$ represents a fluorine atom.

6. A compound according to claim 1 wherein $X^2$ represents a fluorine atom.

7. A compound according to claim 1 wherein $Z^1$ represents a hydrogen atom.

8. A compound according to claim 1 wherein $Z^1$ represents a methyl or an ethyl.

9. A compound according to claim 1 wherein Zhu 1 represents an unsubstituted cyclobutyl.

10. A compound according to claim 1 wherein $Z^2$ and $Z^3$ independently represent a hydrogen atom or a methyl.

11. A compound according to claim 10 wherein $Z^2$ represents a hydrogen atom and $Z^3$ represents a hydrogen atom or a methyl.

12. A compound according to claim 1 wherein $R^1$, $R^2$, $R^3$, $R^4$ and $R^5$, which can be the same or different, represent a hydrogen atom; a halogen atom; substituted or non substituted $C_1$-$C_8$-alkyl; $C_1$-$C_8$-halogenoalkyl comprising up to 9 halogen atoms which can be the same or different; substituted or non substituted $C_3$-$C_7$-cycloalkyl; tri($C_1$-$C_8$-alkyl)silyl; or substituted or non substituted $C_1$-$C_8$-alkylsulfanyl.

13. A compound according to claim 12 wherein the substituent $R^1$ represents a halogen atom; $C_1$-$C_8$-alkyl; $C_1$-$C_8$-halogenoalkyl comprising up to 9 halogen atoms which can be the same or different; $C_3$-$C_7$-cycloalkyl; tri($C_1$-$C_8$-alkyl)silyl or $C_1$-$C_8$-halogenoalkylsulfanyl comprising up to 9 halogen atoms which can be the same or different.

14. A compound according to claim 1 wherein the substitutents $R^1$ and $R^5$, which can be the same or different, represent a halogen atom; $C_1$-$C_3$-alkyl; $C_1$-$C_8$-halogenoalkyl comprising up to 9 halogen atoms which can be the same or different; $C_3$-$C_7$-cycloalkyl; tri($C_1$-$C_8$-alkyl)silyl or $C_1$-$C_8$-halogenoalkylsulfanyl comprising up to 9 halogen atoms which can be the same or different.

15. A fungicide composition comprising, as an active ingredient, an effective amount of a compound of formula (I) according to claim 1 and an agriculturally acceptable support, carrier or filler.

16. A method for controlling phytopathogenic fungi of crops, characterized in that an agronomically effective and substantially non-phytotoxic quantity of a compound according to claim 1 is applied to the soil where plants grow or are capable of growing, to the leaves and/or the fruit of plants or to the seeds of plants.

17. A method for controlling phytopathogenic fungi of crops, characterized in that an agronomically effective and substantially non-phytotoxic quantity of a fungicide composition according to claim 15 is applied to the soil where plants grow or are capable of growing, to the leaves and/or the fruit of plants or to the seeds of plants.

* * * * *